US011925951B2

(12) United States Patent
Leslie et al.

(10) Patent No.: US 11,925,951 B2
(45) Date of Patent: Mar. 12, 2024

(54) EXTENDED-RANGE SPRAY APPLICATOR

(71) Applicant: BOEHRINGER INGELHEIM ANIMAL HEALTH USA INC., Duluth, GA (US)

(72) Inventors: Christopher Davis Leslie, Cleveland, GA (US); Ludovic Porcher, Quilly (FR)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 226 days.

(21) Appl. No.: 17/183,076

(22) Filed: Feb. 23, 2021

(65) Prior Publication Data

US 2021/0197217 A1    Jul. 1, 2021

Related U.S. Application Data

(63) Continuation of application No. 16/690,899, filed on Nov. 21, 2019, now abandoned, which is a continuation of application No. 15/154,082, filed on May 13, 2016, now abandoned.

(60) Provisional application No. 62/161,440, filed on May 14, 2015.

(51) Int. Cl.
| | | |
|---|---|---|
| *B05B 3/10* | (2006.01) |
| *A01K 45/00* | (2006.01) |
| *A61D 1/02* | (2006.01) |
| *A61K 9/00* | (2006.01) |
| *A61K 9/06* | (2006.01) |
| *A61K 35/00* | (2006.01) |
| *A61K 35/741* | (2015.01) |
| *A61K 39/00* | (2006.01) |
| *A61K 39/17* | (2006.01) |
| *A61K 39/215* | (2006.01) |
| *A61M 11/00* | (2006.01) |
| *B01F 23/213* | (2022.01) |
| *B01F 35/32* | (2022.01) |
| *B01F 101/00* | (2022.01) |
| *B05B 1/28* | (2006.01) |
| *B05B 7/24* | (2006.01) |
| *B05B 9/08* | (2006.01) |
| *C12N 7/00* | (2006.01) |

(52) U.S. Cl.
CPC ............ *B05B 3/1014* (2013.01); *A01K 45/00* (2013.01); *A61D 1/025* (2013.01); *A61K 9/0073* (2013.01); *A61K 9/06* (2013.01); *A61K 35/741* (2013.01); *A61K 39/17* (2013.01); *A61K 39/215* (2013.01); *B01F 23/21311* (2022.01); *B01F 35/32025* (2022.01); *B05B 1/28* (2013.01); *B05B 3/105* (2013.01); *B05B 3/1092* (2013.01); *B05B 7/2416* (2013.01); *B05B 7/2478* (2013.01); *B05B 9/085* (2013.01); *B05B 9/0894* (2013.01); *C12N 7/00* (2013.01); *A61K 2035/115* (2013.01); *A61K 2039/543* (2013.01); *A61K 2039/544* (2013.01); *A61K 2039/552* (2013.01); *A61M 11/00* (2013.01); *B01F 2101/2202* (2022.01); *C12N 2760/18134* (2013.01); *C12N 2760/18171* (2013.01); *C12N 2770/20034* (2013.01); *C12N 2770/20071* (2013.01)

(58) Field of Classification Search
CPC ........ B05B 1/28; B05B 3/1092; B05B 7/2416; A61M 11/00
See application file for complete search history.

(56) References Cited

U.S. PATENT DOCUMENTS

| | | | |
|---|---|---|---|
| 3,460,764 A | | 8/1969 | Wallis |
| 3,714,950 A | * | 2/1973 | Miska .................... A61M 11/00 D28/13 |
| 3,997,115 A | * | 12/1976 | Licudine ............... B05B 7/2464 239/351 |
| 4,270,698 A | | 6/1981 | Bisa et al. |
| 4,589,597 A | | 5/1986 | Robisch et al. |
| 4,936,510 A | * | 6/1990 | Weinstein .............. B05B 3/001 239/290 |
| 5,557,848 A | | 9/1996 | Povey |
| 6,910,446 B2 | | 6/2005 | Johnston, Jr. |
| 2006/0086821 A1 | | 4/2006 | Junkel et al. |
| 2011/0036926 A1 | * | 2/2011 | Nunes ...................... F24F 6/12 239/214 |

FOREIGN PATENT DOCUMENTS

| | | |
|---|---|---|
| CA | 2416726 A1 | 7/2004 |
| GB | 1515511 A | 6/1978 |
| NL | 238022 | 1/1964 |
| RU | 97064 U1 | 8/2010 |

OTHER PUBLICATIONS

UlvaVac (Micron UlvaVac, Merial, Instruction manual for UlvaVac, copyright 2013) (Year: 2013).*
Soares, Roberto, et al. "Spray vaccination: what happens during and after this procedure." Ceva animal health asia 2 (2007): 1-3.
Acevedo-Malavé, Alejandro, and Máximo García-Sucre. "3D coalescence collision of liquid drops using smoothed particle hydrodynamics." INTECH Publishers 5 (2011): 85-106.
FOG Electric Atomizer Sprayer (YouTube.com, 2010, https://www.youtube.com/watch?v=iqL56zZu24l) (Year: 2010).

* cited by examiner

*Primary Examiner* — Mark V Stevens

(57) ABSTRACT

The disclosure relates to an extended-range spray applicator, and methods of making and use thereof, for dosing vaccines and/or probiotics to avian animals at a distance.

15 Claims, 25 Drawing Sheets

Shroud Version 7

Shroud Version 6

EXTENDED-RANGE SPRAY APPLICATOR

CROSS-REFERENCE TO OTHER APPLICATIONS

This application is a continuation of and claims priority to U.S. non-provisional patent application Ser. No. 16/690,899, filed on Nov. 21, 2019, now abandoned; which is a continuation of U.S. non-provisional patent application Ser. No. 15/154,082, filed on May 13, 2016, now abandoned; which is a non-provisional of U.S. provisional patent application Ser. No. 62/161,440, filed on 14 May 2015, now expired. These applications are herein incorporated by reference in their entirety.

RELATED APPLICATIONS/INCORPORATION BY REFERENCE

Any foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any such document in this application is not an admission that such document is available as prior art to the present invention and does not reflect any view of the validity, patentability and/or enforceability of such cited patent documents.

FIELD OF THE INVENTION

The disclosure generally relates to spray applicators for dosing vaccines or probiotics to avian animals at a distance. In particular, the disclosure relates to spray applicators for vaccines (i.e. "sprayers") or probiotics, having increased dosing ranges, relative to prior spray applicators. The disclosed improved spray applicator delivers effective and uniform amounts of liquid vaccine or probiotic formulations, having uniformly distributed droplet sizes, to avian animals from at least about 5 to at least about 10 meters away from the spray applicator.

BACKGROUND OF THE INVENTION

Spray vaccination can be defined as the method for administration of the live vaccines dissolved in water, in the form of droplets, through the air to the birds' target cells. It is considered to be one of the most efficient routes for massive vaccination against Newcastle disease ND and infectious bronchitis IB as it triggers local immunity in the respiratory tract. Moreover, as the respiratory tract is the main site of entry of NDV and IBV, local immediate immune mechanisms therefore form a first line of defense against these infections. Besides that, spray vaccination also induces humoral immune response.

Similarly, spray administration of probiotics can be defined as the method for administration of the probiotics (dissolved in water or another suitable solvent), in the form of droplets, for inhalation or ingestion by the bird so as to modulate the bird's intestinal microbiota and confer a beneficial effect on the health or well-being of the bird. Known probiotic spray applicators, include LEE, Eng-Hong, PCT Publication number WO 2012/016328.

This method of vaccination can be done either in the hatchery with cabinet sprayers or at the farms with different kinds of equipment and it allows the vaccination of a large number of birds in a short period of time with low cost. Nevertheless, it is not always synonymous of efficacy as it can lead to vaccination failures uneven uptake and/or development of post-vaccination reactions PVR if it is not properly managed.

In order to reach the desirable results with the spray process, it is important to consider some key points as the formation of the droplets and the target to be reached respiratory or digestive tract. The spraying process consists of forcing a vaccine solution through hydraulic nozzles using determined pressure, which provides the energy that breaks a stream of water into droplets. More recently, sprayers equipped with spinning disc atomizers have been developed. In any case, the size of the droplets is influenced by pressure, type of nozzle and environment conditions. These droplets can be classified, according to their size at the point of production as atomization or aerosol <50 µm, fine spray 50-100 µm or coarse spray 100-150 µm.

Rotary or disc atomizers generate conical sheets by imparting a tangential velocity component to the flow as it issues from a discharge orifice. The mechanisms of sheet integration are broadly the same as those responsible for jet breakup i.e. in the case of a pressure-sprayer. If the liquid sheet is flowing at high velocity, the turbulence forces generated within the liquid may be strong enough to cause the sheet to disintegrate into groups without any aid or intervention from the surrounding air. However, the principal cause of sheet breakup stems from interaction of the sheet with the surrounding air, whereby rapidly growing waves are superimposed on the sheet. Disintegration occurs when the wave amplitude reaches a critical value and fragments of sheet are torn off. Surface tension forces cause these fragments to contract into irregular ligaments which then collapse into droplets according to the Rayleigh mechanism. Rotary atomizers utilize centrifugal energy to achieve the high relative velocity between air and liquid that is needed for good atomization. A rotating surface is employed which may take the form of a flat disc, vaned disc, cup, bell, or slotted wheel. A simple form of rotary atomizer, comprising a spinning disc with means for introducing liquid at its center. The liquid flows radially outward across the disc and is discharged at high velocity from its periphery. Several mechanisms of atomization are observed with a rotating flat disc, depending on the liquid flow rate and the rotational speed of the disc. At low flow rates the liquid is discharged from the edge of the disc in the form of droplets of fairly uniform size.

The UlvaVac™ is a professional spray applicator for poultry vaccination FIG. 1A/1B, and the UlvaVac™ Instruction Manual 9010, rev 2, which is herein incorporated by reference in its entirety. The spray applicator incorporates a spinning disc atomiser see above discussion to control accurately spray droplet size, a process referred to as Controlled Droplet Application CDA which is essential for the efficient delivery of spray vaccine. Rotary/spinning disc atomisers are disclosed in a variety of documents, particularly in U.S. Pat. No. 5,557,848 A to Micron Sprayers Limited. Spray droplets are dispersed in a turbulent airstream to ensure even distribution to all birds.

The spray applicator consists of a one litre spray reservoir, colour coded liquid feed nozzles to control flow rate, atomiser spray head with spinning disc, electrically operated fan to disperse spray and a 12 V battery for power with recharging unit. The UlvaVac can be used for vaccination of broilers, layers and turkeys and is recommended for vaccination against respiratory diseases such as Infectious Bronchitis, Turkey Rhinotracheitis and Newcastle Disease.

Low spray volumes of 1-2 litres per house are normally applied allowing operators to treat up to 30,000 broilers, for example, in less than 20 minutes. The method of atomisation used by the UlvaVac gives precise control over droplet size, ensuring accurate delivery of vaccine to the eye and upper respiratory tract. Post-vaccinal reaction caused by the production of very small droplets is minimised. The precise control over droplet size also allows the use of low spray volumes which significantly reduces the time spent for both vaccine preparation and application, ensuring minimal disturbance to birds.

The spray droplet sizes produced by the UlvaVac have been accurately measured. The spray applicator is capable of producing a very uniform size range of droplets suitable for the delivery of respirable spray vaccines. Spraying should be carried out on a time and volume basis rather than solely a volume per thousand birds. The more time spent spraying the birds the better the vaccine coverage. However, the time allowed for spraying is determined by the length of time during which the shed/house ventilation can be inoperative. Nozzles may be selected to accommodate different applications.

TABLE 1

Different rotating disc nozzles provide different flow rates

| Nozzle | Flow Rate | Spray volume ml applied in | | |
| --- | --- | --- | --- | --- |
| | | 10 min | 15 min | 20 min |
| Yellow | 45 ml/min in | 450 | 675 | 900 |
| Orange | 60 ml/min in | 600 | 900 | 1200 |
| Red | 90 ml/min in | 900 | 1350 | 1800 |
| Black | 150 ml/min in | 1500 | 2250 | 3000 |

To spray a house containing 30,000 ten day old broilers, depending on ambient temperature, the ventilation can be shut down for approximately 20 minutes without stressing the birds. In 20 minutes the yellow nozzle will spray approximately 900 ml. 30,000 doses should be mixed in 900 ml of fresh distilled water and the vaccine sprayed on the birds for 20 minutes.

To spray a house containing 8,000 twelve week old broiler breeders, depending on ambient temperature, the ventilation can be shut down for approximately 20 minutes without stressing the birds. In 20 minutes the yellow nozzle will spray approximately 900 ml. 8,000 doses of vaccine should be mixed in 900 ml of fresh distilled water and the vaccine sprayed on the birds for 20 minutes.

The UlvaVac provides the uniform droplet size required for vaccinating avian animals including chickens, including broilers, but its range is limited i.e. the user must be relatively close to the birds. Before the instant disclosure, it was not known whether the dosing range could be extended by increasing the speed of the air flow. For example, if increasing the speed of the air flow caused the vaccine droplet size to become too small, the vaccine would end up in the lungs of the birds, which is not desirable. Furthermore, if higher speed caused the vaccine to be sprayed non-uniformly, some of the birds would be under-protected, while others would be over-dosed, and suffer from side effects. Finally, higher air speeds could also comprise the immunogenicity and/or efficacy of the vaccine or probiotic formulation itself.

Therefore, to achieve the desired range increase for spray applicators, it would be necessary to increase the speed of airflow, while taking into account and optimizing at least four variables: 1 air flow geometry; 2 uniformity of droplet size; 3 uniformity of vaccine dose delivered to each bird; and 4 preservation of the immunogenicity of a vaccine that subjected to high air flow conditions. Development of tests to measure each of these variables is also required for the development of an improved dosing range spray applicator.

ADVANTAGES

Like the UlvaVac, the disclosed extended-range spray applicator is battery powered. As well as spinning the disc atomizer that produces the uniform droplets, the battery also powers an air supply means, which may be a blower motor. The combined action of the air supply means and the rotating disc atomizer distributes the vaccine over an area of up to about 5 to about 10 meters long and 2 meters wide. The about 5 to about 10 L of liquid that is contained in the machine's reservoir should last about 10 to about 30 minutes when a yellow nozzle is used.

For broilers, protection from good spray vaccination reduces the possibility of economic losses caused by diseases that enter via the respiratory tract and can cause weight loss and general poor performance of the flock. For layers and breeders, as well as respiratory disease, Infectious Bronchitis viruses can damage the kidneys and oviduct with infections resulting in false layers, drops in production and poor quality eggs.

By using the instantly disclosed extended-range spray applicator, specifically for use in poultry, vaccines and probiotics are delivered directly to the upper respiratory system—including the eye, nasal cavities and trachea. The device yields a uniform droplet size, is not too heavy to use and is battery powered so it is not too noisy for the birds. Similarly, using the instantly disclosed extended-range spray applicator for administering probiotics enables a predetermined dose of liquid probiotic to be sprayed directly on the birds. It is expected that as the birds preen they will ingest the probiotics from their feathers.

If a vaccine is sprayed at "chicken-height," not only will pullets and broilers inhale the vaccine or probiotic, it will also go into the Harderian gland in the eye, thereby stimulating the birds' immune systems. Similarly, if the probiotic is sprayed at "chicken-height," it enables the efficient delivery of the probiotic to the bird so that they can ingest probiotics from their feathers when they preen.

When one applies vaccines or probiotics with the disclosed improved spray applicator, the band of spray is about 1 to about 2 meters wide and goes about five (5) to about ten (10) meters out, so it can cover a large number of birds. It is possible to vaccinate and/or administer probiotics to 100,000 birds in just 20 minutes.

The ventilation should be turned off prior to vaccinating the birds using the disclosed improved spray applicator. If there is a lot of air movement, the vaccine can get blown away by the ventilation system.

IB vaccines and probiotics are quite fragile, so when poultry producers reconstitute the vaccine or probiotic, they must vaccinate and/or administer the probiotic to the birds as quickly and effectively as possible. If an IB vaccine is put through drinker lines, it can take the birds more than two hours to drink it all so a lot of the vaccine virus will have died before it has been consumed by the birds. Similarly, administration of probiotics through drinker lines is known to be problematic as the liquid may be spilled by the birds or the probiotic settles in the lines and does not result in even distribution to the flock.

SUMMARY OF THE INVENTION

An object of the present disclosure is to provide an extended-range spray applicator and methods of making and use thereof. The extended-range spray applicator is particularly well-suited to delivering liquid medicament, including vaccines and/or probiotics, via an array of droplets having an average droplet size of from about 50 μM to about 200 μM in diameter. These droplets sizes are particularly useful for vaccinating avian animals, including chickens, against a variety of respiratory pathogens or administering probiotics to birds. The spray applicator is capable of vaccinating or administering probiotics to avians at a distance of at least about 5 to about 10 meters.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures, wherein:

FIG. 4C shows a front view of the head assembly 20, having the shroud air guide 22, the nozzle 32 and the rotating disc atomizer 23a;

DETAILED DESCRIPTION OF THE INVENTION

Figure 1:
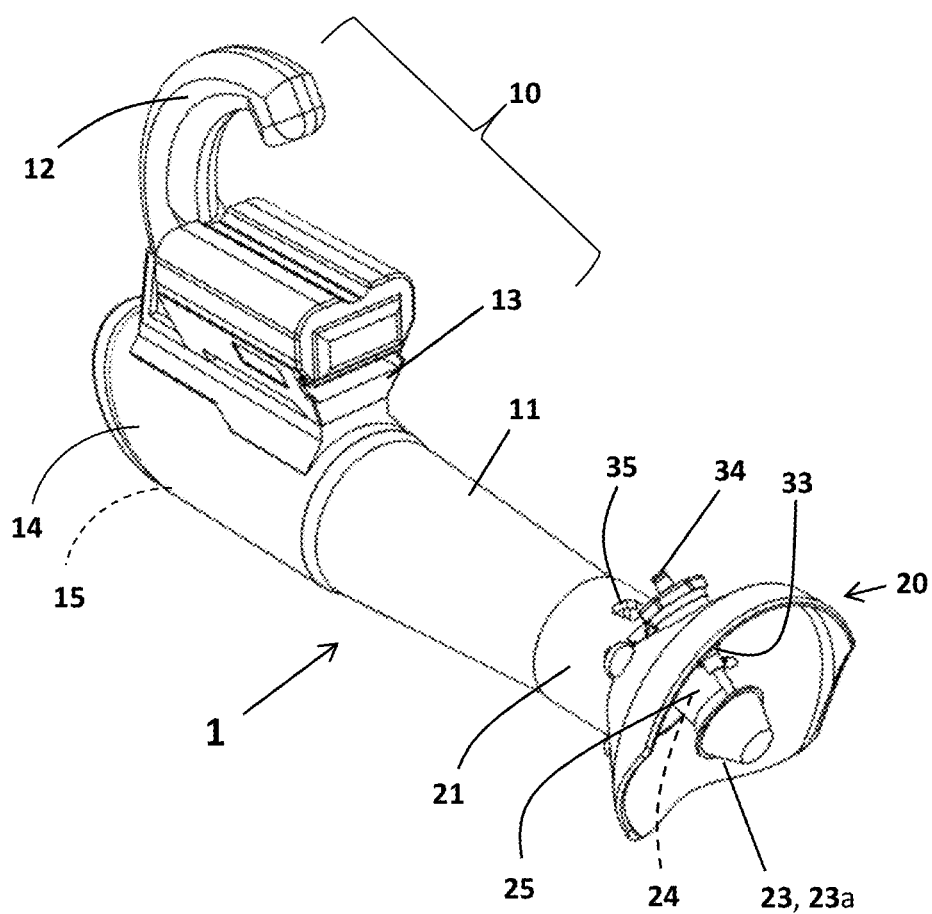
FIG. 1 shows an extended-range spray applicator 1 according to the invention.

The present invention relates to extended-range spray applicator and methods of making and use thereof. The extended-range spray applicator is particularly well-suited to delivering liquid medicament, including vaccines and/or probiotics, via an array of droplets having an average droplet size of from about 50 µM to about 200 µM in diameter. These droplets sizes are particularly useful for vaccinating avian animals, including chickens, against a variety of respiratory pathogens or administering probiotics to birds.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this disclosure. To the extent the definitions of terms in the publications, patents, and patent applications incorporated herein by reference are not the same as the definitions set forth in this specification, the definitions in this specification control for the entire specification, including the claims. Any other definitions in the publications, patents, and patent applications incorporated herein by reference that are not explicitly provided in this specification apply only to the embodiments discussed in the publications, patents, and patent applications incorporated herein by reference.

As used above, and throughout the description of the invention, the following terms, unless otherwise indicated, shall be understood to have the following meanings:

As used herein, the singular forms "a", "an" and "the" are intended to include the plural forms as well, unless the context clearly indicates otherwise.

The term "and/or" as used herein includes any and all combinations of one or more of the associated listed items.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The term "effective amount" as used herein means an amount of a composition according to the present invention effective in producing the desired veterinary effect.

In an aspect, the disclosure provides an extended-range spray applicator substantially as depicted in FIG. 1 or FIGS. 2A-2D.

In some embodiments, the extended-range spray applicator comprises:
  (a) an air supply means, for providing a flow of air through the spray applicator; wherein the air supply means is configured to connect to
  (b) a head assembly, configured to attach to the air supply means; wherein the assembly comprises:
    (i) an air supply means adaptor, for connecting the head assembly to the air supply means;
    (ii) at least one air guide shroud, to guide the flow of air coming from the air supply means;
    (iii) a liquid atomizer means, for transforming liquid into sub-millimeter-sized droplets; wherein the atomizer is situated centrally within the shroud;
    (iv) a mounting means, for attaching the atomizer to the head assembly;

(v) a motor, mechanically connected to the atomizer; and optionally (vi) a battery receptacle, for holding a battery, which is electrically connected to the motor.

In some embodiments of the spray applicator, the head assembly, already equipped with a primary shroud, is configured to reversibly attach to a secondary shroud.

In some embodiments, the mounting means are extenders, and both shrouds comprise slots through which the extenders pass.

In some embodiments, the atomizer is fixedly connected to the extenders.

In other embodiments, the atomizer is adjustably connected to the extenders, such that a user may direct the atomizer upward or downward, with respect to the direction of air flow.

In some embodiments, the adjustable connection also allows the user to position the atomizer laterally, such that it is either nearer to, or farther from, the air supply means.

In some embodiments, both the primary and secondary shrouds comprise a plurality of spacers, which are configured to allow the shrouds to be reversibly connected to one another. For example, each shroud may comprise 4 spacers.

In some embodiments, the air supply means adapter is cylindrical and comprises a means for lockably attaching the head assembly to the air supply portion of the spray applicator.

In some embodiments, the spray applicator comprises a battery housing, situated atop the head assembly, and configured to receive and house a rechargeable battery, which supplies electricity to the atomizer motor.

In some embodiments, the atomizing means is a rotary disc atomizer, which is mechanically connected to a disc atomizer motor, which is housed within a motor housing, which is fixedly connected to a disc atomizer assembly frame.

In another aspect, the disclosure provides a head assembly, for use with the disclosed spray applicator, comprising:
  (a) an air supply means adaptor, for connecting the head assembly to the air supply means;
  (b) at least one air guide shroud, to guide the flow of air coming from the air supply means;
  (c) a rotary disc atomizer, for transforming liquid into sub-millimeter-sized droplets; wherein the atomizer is situated centrally within the shrouds;
  (d) at least two extenders, for attaching the atomizer to the head assembly;
  (e) a motor, mechanically connected to the atomizer; and
  (f) a battery receptacle, for holding a battery, which is electrically connected to the motor.

In an embodiment, the head assembly may comprise a primary and secondary shroud, each comprising a slot through which the extenders pass. In an advantageous embodiment, the secondary shroud has a conical angle of about 30°.

In some embodiments of the head assembly, at least one shroud is characterized by having at least three diameters, D1, D2 and D3, and at least two angles, A1 and A2.

In some embodiments, D1 is at least about 30% to about 50% smaller than D2, and D2 is about equal to or is about 10% smaller than D3.

In some embodiments, A1 is between about 90° and about 145°, and A2 is between about 130° and 160°.

In some embodiments, the spray applicator is capable of delivering to an avian animal in need thereof a safe and effective amount of a liquid medicament selected from an immunological formulation, a vaccine or probiotic formulation, an antibiotic formulation, an antifungal formulation, an anticoccidial formulation, a feed additive formulation and combinations thereof.

In some embodiments, the spray applicator is configured to transform the liquid medicament into substantially uniformly sized droplets, with 90% of the droplets having a diameter between about 25 µm and about 200 µm.

In other embodiments, the spray applicator is capable of propelling fluid/vaccine or probiotic droplets at least about 5 or about 10 meters through the air, to deliver safe and effective amounts of the droplets to the avian animals.

In some embodiments, the spray applicator comprises:
  (a) an air supply means, which is operably connected to
  (b) a head assembly, which comprises an air supply means adapter, configured to sealably connect the head assembly to the air supply means; comprising:
    (i) at least one air shroud guide, for guiding the array of droplets to the avian animals; and
    (ii) a liquid medicament atomizing means, for transforming the liquid medicament into a uniform distribution of droplets.

In some embodiments, the air shroud guide and the air supply means adapter are either a unitary piece or are at least two separate pieces, to accommodate connection of the head assembly to many different types of air supply means.

In some embodiments, the air supply means is a commercially-available blower, including a leaf blower.

In some embodiments, the atomizing means is a rotary disc atomiser, which is operably connected to an electric motor. In an alternate embodiment, the rotary disc atomizer is operably connected to an impeller, which is driven by the air flowing from the air supply means, and which turns the rotary disc atomizer in place of an electric motor.

In some embodiments, the disc assembly comprises a disc atomizer, a washer and a disc fixing screw. The disc atomizer comprises grooves, wherein the spinning of the atomizer by the motor causes liquid to be drawn into and through the grooves, and wherein the force of the spinning causes the liquid to exit the atomizer as an array of droplets dispersed throughout a substantially columnar or conical flow of air.

In some embodiments, the head assembly shroud is characterized by having at least three diameters, D1, D2 and D3, and at least two angles, A1 and A2.

In some embodiments, D1 is at least about 30% to about 50% smaller than D2 and D2 is about equal to or is about 10% smaller than D3.

In some embodiments, A1 is between about 90° and about 145° and A2 is between about 130° and 160°.

In another aspect, the disclosure provide a method of vaccinating avian animals against respiratory pathogens, from a distance of at least about 5 or about 10 meters away, comprising the step of using the disclosed extended-range spray applicator to administer to said avian animals an effective amount of at least one respiratory antigen, carried in the form of uniformly-sized droplets, having diameters of from about 50 µm to about 200 µm, thereby vaccinating said avian animal.

In some embodiments, 10,000 avian animals are vaccinated and/or administered probiotics in less than about 20 minutes; and/or about 5 L to about 10 L of vaccine is delivered within about 20 minutes.

In some embodiments, the disclosure provides a method of treating birds with a probiotic formulation therapeutic agent by dispersing the probiotic formulation in the form of uniformly-sized droplets, having diameters of from about 50 µm to about 200 µm, from a spray applicator of claim 1 or 2, wherein the birds being treated are at least about 5 to at least about 10 meters away from the spray applicator; and allowing the birds to consume the droplets.

In some embodiments, the probiotic formulation is a liquid or liquid-like gel.

In other embodiments, 10,000 birds are treated in less than about 20 minutes, and/or about 5 L to about 10 L of probiotic formulation is delivered within about 20 minutes.

DETAILED DESCRIPTION OF THE PREFERRED EMBODIMENT

Referring now in more detail to the drawings, in which like numerals indicate like parts throughout the several views, FIG. 1 illustrates a front perspective view of an extended-range spray applicator 1. The extended-range spray applicator 1 comprises the following components: an air supply means 10, which is operably connected to an air supply conduit 11, and a handle/gripping means 12, a rechargeable battery retaining means 13 an air supply blower motor housing 14, and a blower motor 15, which is encased inside the blower motor housing 14; and, an extended-range sprayer head assembly 20. The head assembly 20 comprises an air supply means adapter 21; configured to connect the air supply conduit 11 to a shroud air guide 22; an atomizer means 23, shown here as a rotating disc atomizer 23a; a means for rotating the atomizer 24, where mechanical atomizers are employed; a housing 25 for encasing said atomizer rotating means; a fluid supply conduit 33 for delivering fluid to the atomizer 23. The fluid supply conduit may have a quick-connect adapter 34, for connecting to a second fluid supply conduit 39, which is in fluid communication with a reservoir 40 containing a liquid formulation, including a vaccine or probiotic formulation.

Figure 2A:
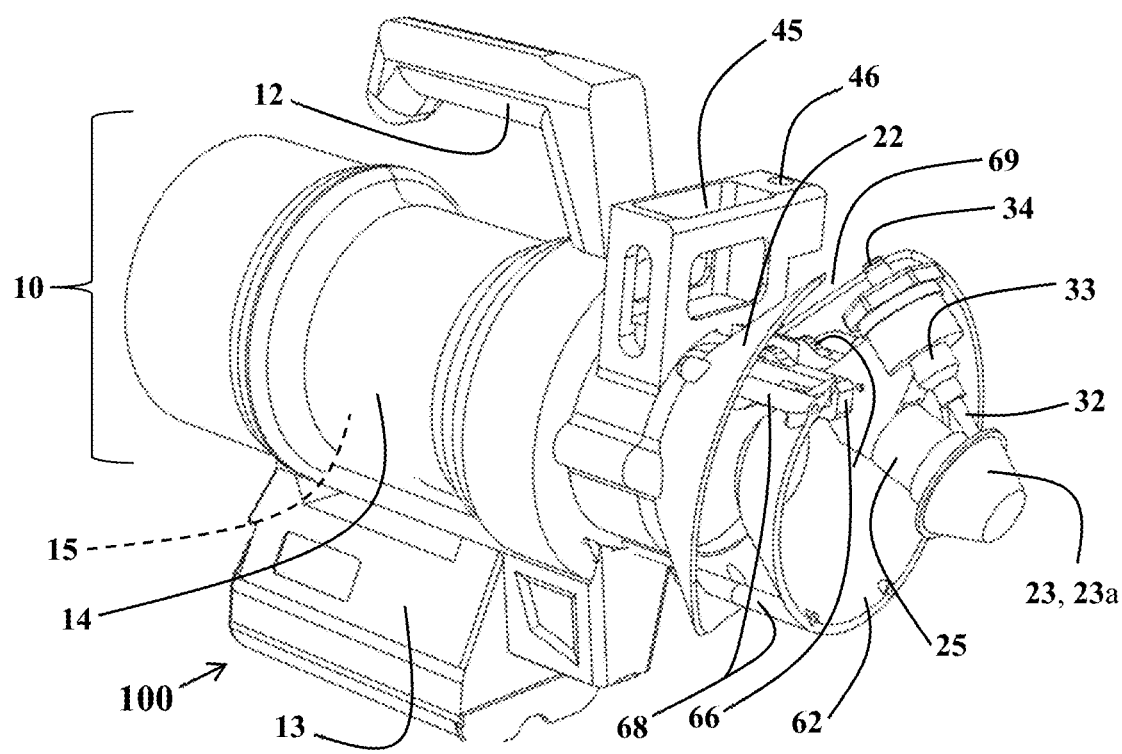
FIG. 2A shows a more compact embodiment 1A of the extended-range spray applicator.

FIG. 2A presents a significantly more compact embodiment of an extended-range vaccine spray applicator 100. In this embodiment, the vaccine spray applicator 100 comprises a compact air supply means 10, which comprises an air-moving means, which may take the form of a plurality of turbine- or fan-style blades 16, operably connected to an air supply motor 15 contained within a housing 14. A handle 12 may be attached in any suitable location on the spray applicator 100, and particularly, mounted atop the motor housing 14, in order to provide, advantageously, excellent user ergonomics. The air supply means 10 is configured to receive a battery retaining means 13, which is electrically connected to the motor 15, which actuates the air moving means 16 to move air through the spray applicator 100 to ultimately propel liquid droplets through the air. A blower on/off switch may be positioned anywhere on the spray applicator, including on the handle 12. Further, the spray applicator 100 may be configured to allow for on-device blower motor battery recharging, or, the battery may be charged using a remote docking station. Various configurations are possible now that the instant disclosure has been made.

Figure 2B:
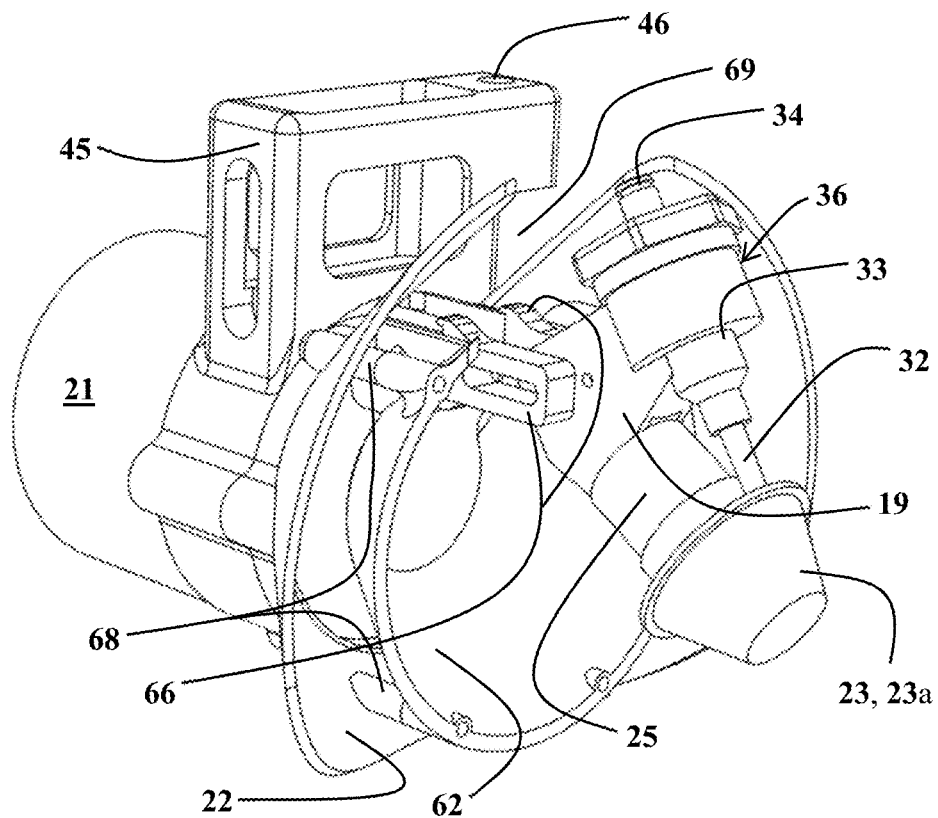
FIG. 2B shows an enlarged view of the head assembly 20 configured to attach to the spray applicator depicted in FIG. 2A. This head assembly 20 comprises "Shroud Version 7," which is comprised of a primary shroud 22 and a secondary shroud 62. In a particular embodiment, the secondary shroud 62 is in approximately in the shape of a section of a 30° cone.
Figure 2C:
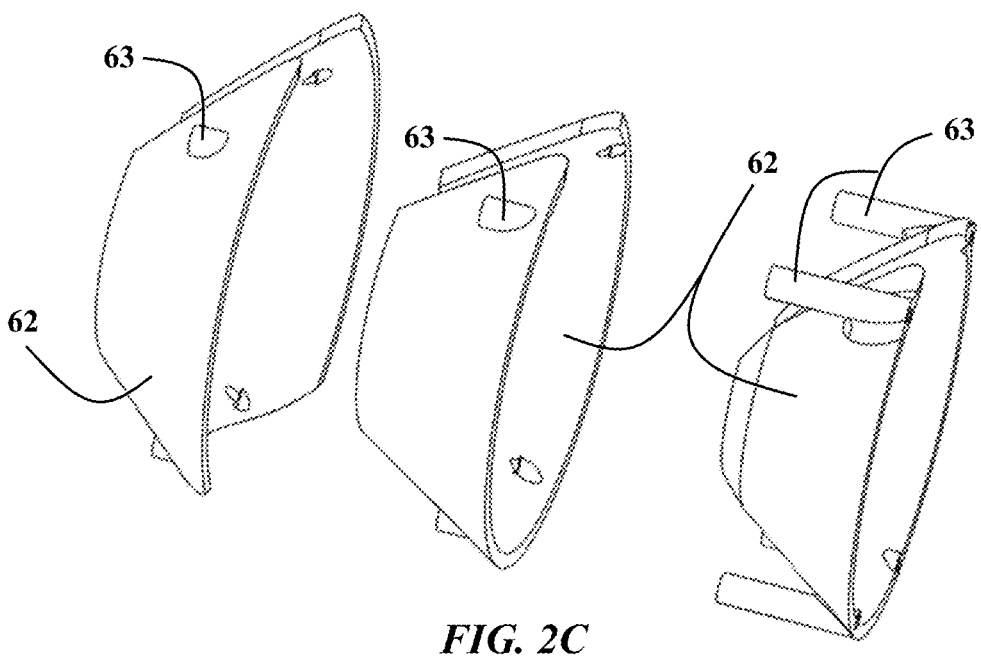
FIG. 2C shows multiple representative secondary shrouds/cones 62, each having different shapes, angles and diameters. The primary shroud 22 and secondary shroud 62 each comprise a slot 69, through with the atomizer extenders 66 may pass.
Figure 2D:
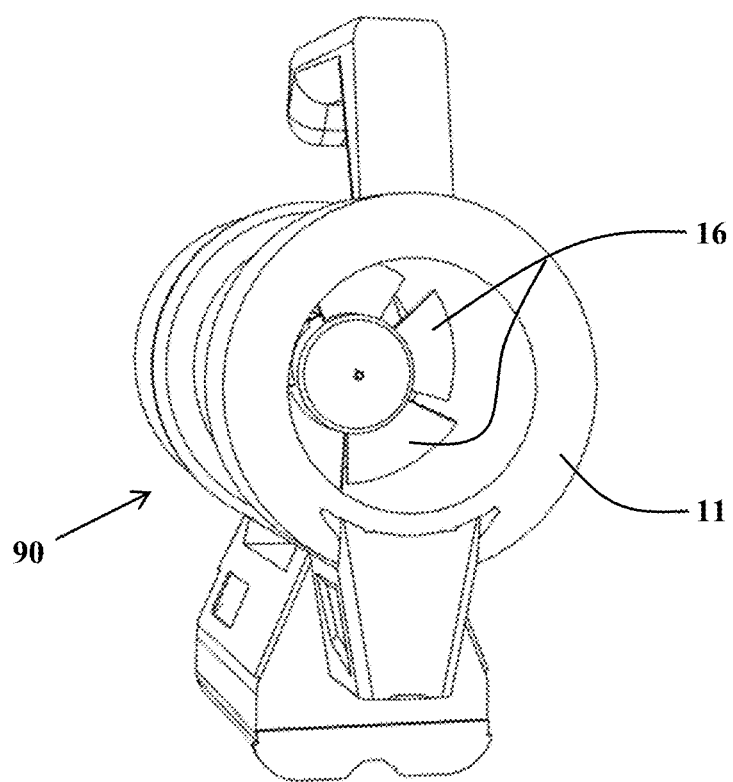
FIG. 2D shows an air supply means 90 with the head assembly 20 removed.

As further shown in FIG. 2B, the spray applicator 100 comprises a head assembly 20, configured to reversibly and sealably engage with the portion of the spray applicator 100 that supplies the air. FIG. 2C presents the head assembly 20 separated from the air supply portion 90, and FIG. 2D shows various possible secondary shrouds 62. Shrouds may be alternately referred to as "cones" or "air guide cones" or "air guide shrouds." In each case, the function of these shrouds 62 is to guide the flow of air to propel atomized liquid droplets that emanate from the atomizer means 23, 23a. FIG. 2D shows the air supply portion 90 of the spray applicator 100 without a head assembly 20 attached thereto. Air supply conduit 11 (which corresponds to the air supply conduit 11 depicted in FIG. 1) is configured to reversibly engage with and/or connect to the air supply portion 90 of the various possible head assemblies 20. Likewise, the head assembly 20 of FIG. 2B is configured to attach to air supply conduit 11 via the air supply means adapter 21. As shown, the air supply means adapter 21 may be cylindrical and may further comprise various means for lockably attaching to the air supply portion 90, such that the force of the moving air will not dislodge the head assembly 20.

Adjacent to the adapter 21, and situated atop the head assembly 20, is a battery housing 45. The battery housing 45 is configured to receive and house a rechargeable battery, which supplies electricity to an atomizer motor, which is electrically connected to the battery, and which is contained within a housing 25. The motor is operably connected to a disc atomizer 23a, and may be activated by turning on a power switch housed in power switch receptacle 46. The disc atomizer 23a and disc atomizer motor 24 are fixedly connected to a disc atomizer assembly frame 19, which itself is fixedly connected to a disc atomizer fluid supply assembly 36. An external fluid supply may be attached and thereby fluidly connected to the supply assembly 36 via quick-connect 34. Any suitable conduit 39 may be connected to quick-connect 34, and the fluid supply may be under pressure using gravity (i.e. by maintaining a fluid reservoir 40 at a suitable height above the sprayer's point of use) or, by using a suitable pumping means, including a pulsatile pump or other fluid pump.

The disc atomizer assembly frame 19 is configured to be fixedly or adjustably mounted to the head assembly 20 via disc atomizer assembly extenders 66, which are configured to allow reversible attachment of multiple different primary 22 and secondary 62 shrouds. When the disc atomizer assembly frame 19 is adjustably connected to the extenders 66, the atomizer assembly may be adjusted up or down, to allow the fluid/vaccine to be delivered at either a higher or lower angle, with respect to the stream of air emanating from the air supply means. The frame may also be adjusted to be either nearer to, or farther away from, the air supply portion 90. This adjustability feature allows the user to select multiple different secondary cones 62, each cone providing a different pattern of fluid/vaccine droplet delivery. Furthermore, this adjustability allows a user to fine-tune and/or customize the spray applicator to suit a variety of different field vaccination conditions. For example, the atomizer 23a may be adjusted to point up to direct the vaccine or probiotic droplets to travel higher and farther. Many different combinations and permutations are possible, now that the disclosure has been made.

Moreover, as shown in FIGS. 2B/2C, the primary shroud/cone 22 and secondary shroud/cone 62 comprise slots 69, which provide space for the disc atomizer assembly extenders 66. The secondary shroud 62 may be placed nearer to, or farther from, the air supply portion 90, depending upon the length of the spacers 63. The longer the spacers 63, the greater the distance between the air supply 90 and the secondary cone 62. And hence, the greater the distance away from the air supply must the disc atomizer frame 19 must be adjusted on the extenders 66. The primary shroud 22 comprises its own spacers 66, which are adapted to receive and connect to the spacers 63 present on the secondary shrouds 62. Configured in this way, the head assembly 20 is adapted to receive a wide variety of different secondary shrouds 62, which provide the user with a significant degree of flexibility in directing the flow of vaccine or probiotic droplets.

Accordingly, the spray applicators 1, 100 offer a dramatic improvement in the field of spray vaccination, significantly increasing each of the following delivery parameters: effective range, speed, accuracy and precision.

Figure 11:
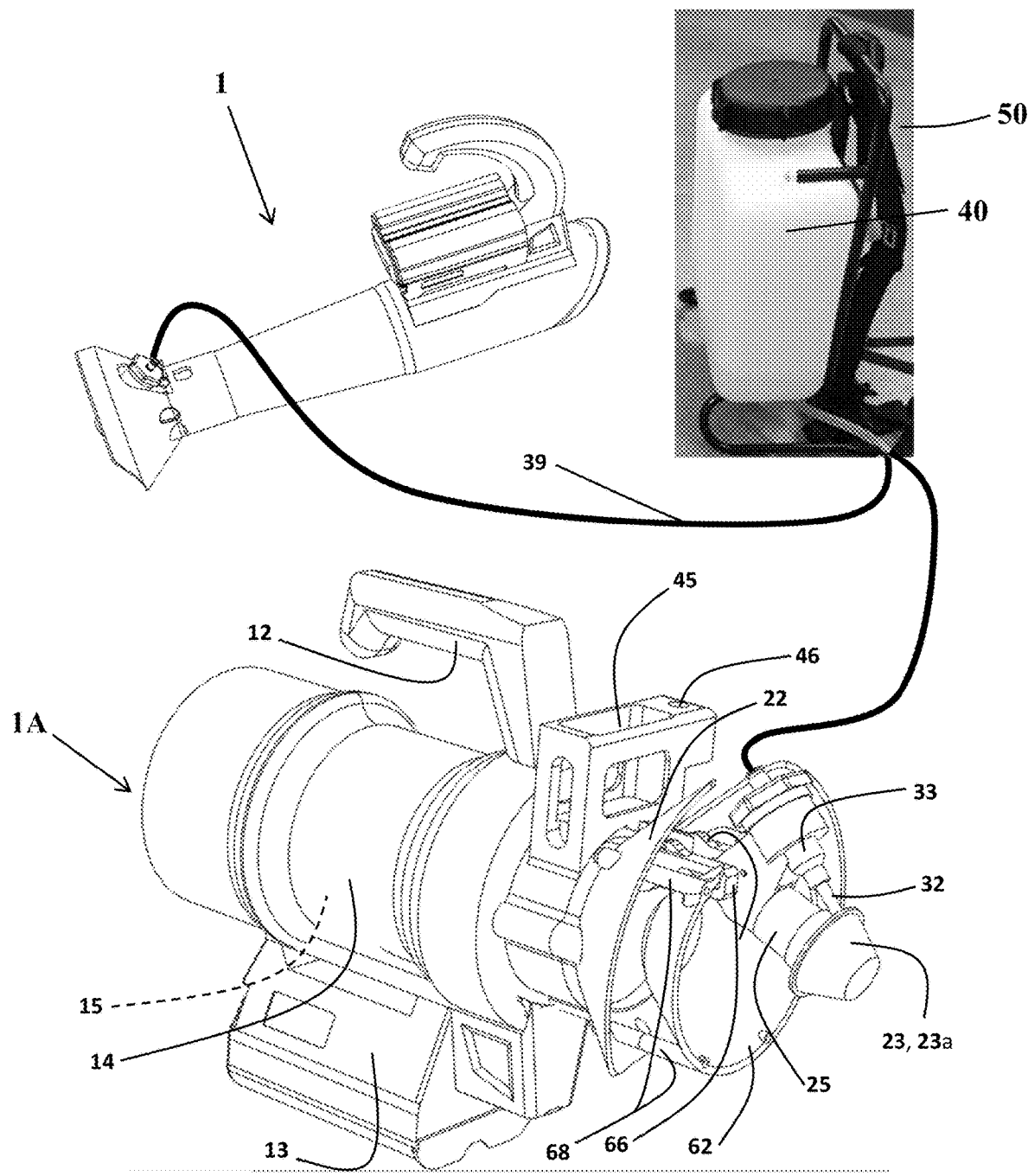
FIG. 11 shows how either a longer spray applicator 1 or a more-compact spray applicator 1A may be fluidly connected to a reservoir 40, which is configured to be secured and held by a wearable, backpack-style reservoir holding assembly 50.
Figure 12:
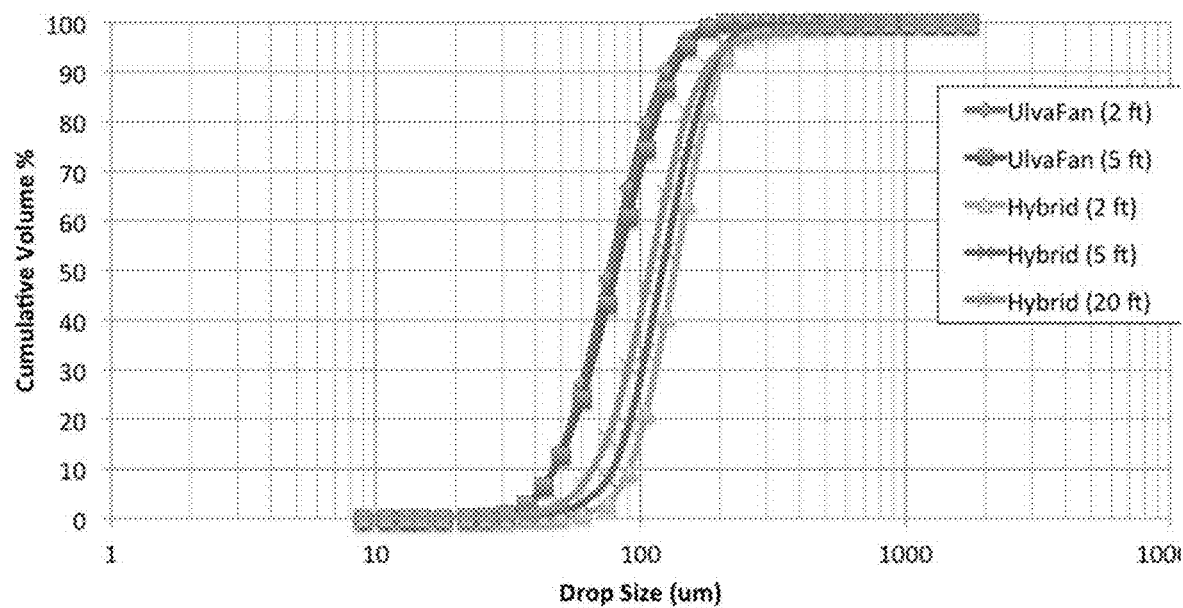
FIG. 12 is a graph showing cumulative volume % v. droplet size. The lines show the prior art UlvaFan at 2 and 5 feet and the "Hybrid" extended-range spray applicator of the instant disclosure. Surprisingly, ideal droplet size is maintained even at 20 feet.

As shown in FIG. 11, the extended-range spray applicator 1, 100 may also be equipped with the sprayer head assembly 20 depicted in FIGS. 10A-10D. Further, the spray applicator 1, 100 is configured to be equipped with a second fluid supply conduit 39, which is configured to be in conditional fluid communication with a fluid reservoir 40. In other words, the fluid supply may be reversibly interrupted by the user of the spray applicator. The fluid may also be pushed through the conduit to the sprayer by action of gravity or a pumping means. In an embodiment, the reservoir 40 is configured to be reversibility attachable to a backpack-style harness assembly which may be worn by a user to facilitate use of the extended-range spray applicator 1, 100. The rechargeable battery means may provide power to both the air supply means and the atomizer means. In one example, an Allied Electronics NTE1936 integrated circuit positive voltage regulator and a 100 microfarad in-line capacitor may be employed to step-down a 40 volt battery to provide 12 volts to the electric motor that is operably connected to the rotating disc atomizer. In an advantageous embodiment, the atomizer motor 15 is electrically connected to, and powered by, a rechargeable battery housed in receptacle 45.

In one embodiment, the probiotic formulation may be in the form of a liquid-like gel. A "liquid-like gel" as used herein is a gel that is easily disrupted or thinned, and that liquefies or becomes less gel-like and more liquid-like under stress, such as caused by the gel being drawn into, through and out of the spinning atomizer, but which quickly returns to a gel when the movement or other stress is alleviated or removed, such as when movement of the fluid exiting the spinning atomizer is stopped, as for example when the exiting fluid lands on the targeted bird. The skilled person knows how to make a formulation more the gel-like or liquid-like by adjusting the amount of gelling agent used in the formulation. One type of liquid-like gel suitable for use in delivering probiotics to birds is disclosed in Wright et al, PCT patent publication number WO2001095891. Other suitable liquid-like gels for use to deliver probiotics to birds include GroGel™ by MS BioScience of Madison, Wis, and gel-Pac™ Animal Science Products, Inc. PO Drawer 631408 Nacogdoches, TX.

In another embodiment, the liquid-like gel pass through the atomizer disc of the spray applicator and thereby dispersed from the spray applicator in the form of small gel beadlets. The term "beadlet" as used herein refers to small discrete particles, which have a mean particle size from about 50 µM to about 200 µM in diameter and are usually nearly spherical. Beadlets contain one or more probiotics in an encapsulated form.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims. This invention includes all modifications and equivalents of the subject matter recited in the aspects or claims presented herein to the maximum extent permitted by applicable law.

It is further noted that it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO ((35 U.S.C.) 112, first paragraph) or the EPO (Article 83 of the EPC), such that Applicants reserve the right and hereby disclose a disclaimer terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

The invention will now be further described by way of the following non-limiting examples.

EXAMPLES

Below disclose the development of the extended-range spray applicator, up to and including the present preferred embodiment, which is detailed above.

Example 1—Shroud Version 1

During development of the first shroud version, the goal was to define an optimum angle for the spinning disk atomizer 23a relative to the air supply/blower tube 11, to provide optimal operation of the spinning disc atomizer 23a. Testing demonstrated that the angle between the tip of the spinning disc and the tube needed to be about 240° to allow the fluid to be siphoned out correctly and to prevent leakage during normal operation. During testing of this first shroud version FIG. 5, it became apparent that some droplets were being carried downstream by the airflow. However, a large percentage of the droplets created by the atomizer disc were being propelled i.e. via centripetal acceleration outside the effective range of the air being pushed by the air supply means i.e. the cylinder of air being pushed through airs supply conduit 11. As such, many droplets were landing only a few feet from the device approx. 3 to 5 feet, which would cause a significant amount of vaccine and/or probiotic to be wasted. It was further observed that the reservoir/bottle made the device very "end-heavy" when full of water or similar solvent. This weight forced the device to have a natural downward aim when held at arm's length. This was observed to be a negative attribute as this would be uncomfortable for the operator to keep the device level for optimum spray coverage. Even were the reservoir to be relocated instead of being mounted directly onto the head assembly 20, the shroud air guide 22 had too small a diameter D3 to capture a sufficient percentage of the spray droplets generated by the disc atomizer 23a.

Example 2—Shroud Version 2

Figure 6A:
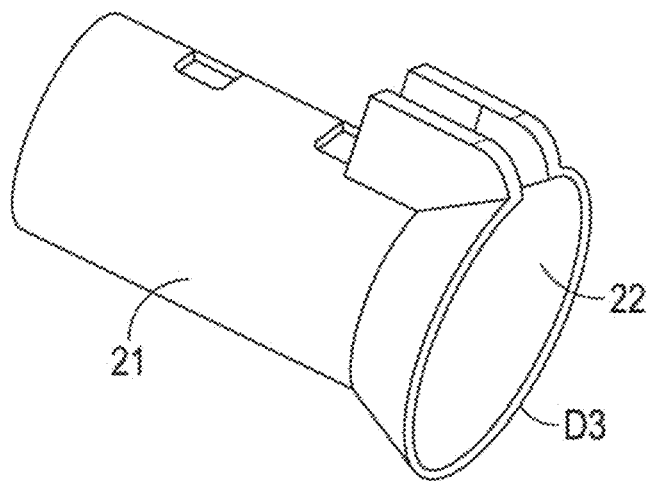
FIG. 6A shows a three-quarter side view of another head assembly 20.
Figure 6B:
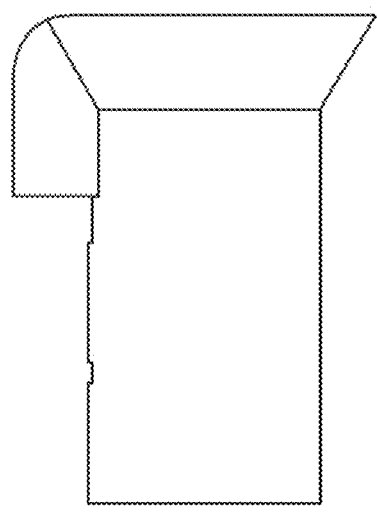
FIG. 6B shows a side cross-section of the head assembly 20 of FIG. 6A.
Figure 6C:
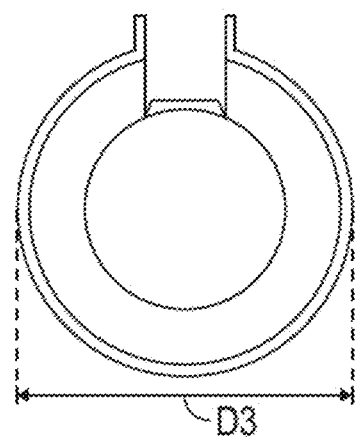
FIG. 6C shows a bottom cross-section of the head assembly 20 of FIG. 6A.

In Version 2 (FIGS. 6A-6C), the onboard vaccine bottle was replaced by a backpack style tank FIG. 11, reservoir 40 to improve the weight and overall ergonomics of the spray applicator. An adapter was designed to adapt the atomizer to a quick connect fitting 34 and silicone supply line 39 from a backpack 50 holding a tank with a capacity of, for example, 5 or 10 liters. The shroud air guide 22 to tube 11 angle was increased to 150°, which resulted in a larger 4.8 inch third shroud diameter D3. This increase in D3 diameter only slightly increased the percentage of droplets captured by the air flow, necessitating further increases to obtain the required vaccine and/or probiotic delivery.

Example 3—Shroud Version 3

Figure 7A:
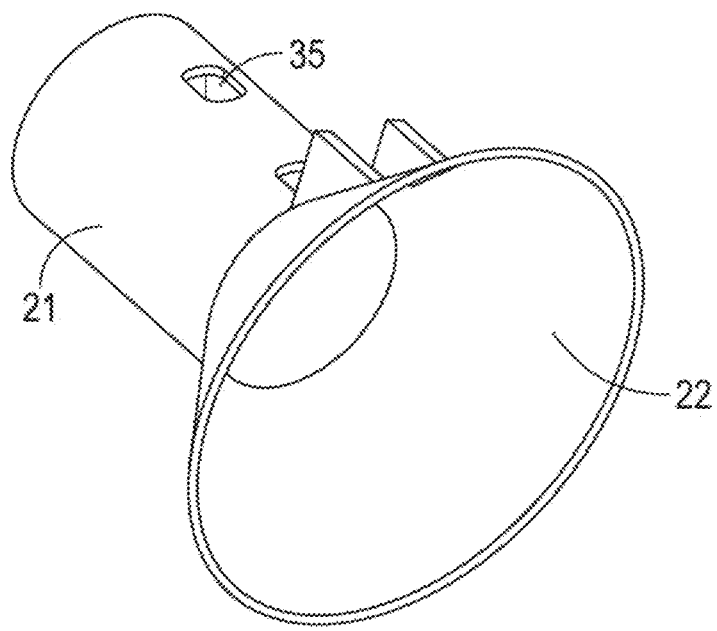
FIG. 7A shows a three-quarter side view of another head assembly 20.
Figure 7B:
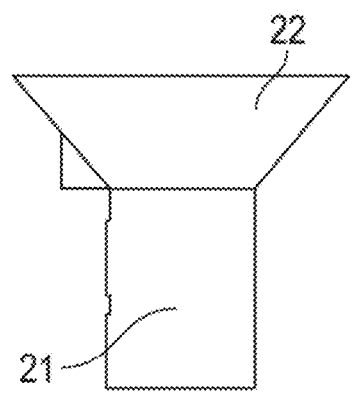
FIG. 7B shows a side cross-section of the head assembly 20 of FIG. 7A.
Figure 7C:
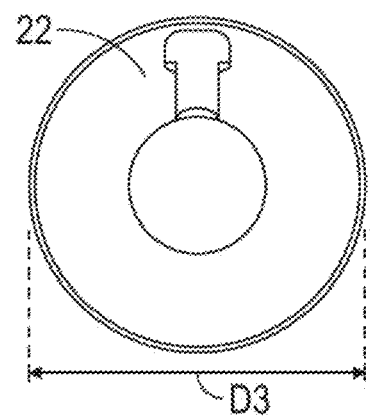
FIG. 7C shows a bottom cross-section of the head assembly 20 of FIG. 7A.

In Version 3 (FIGS. 7A-7B), angle A2 was increased to 140°, and the shroud was lengthened to about 2.6", which resulted in a much larger about 7.6" diameter shroud air guide 22. This D3 diameter increase resulted in substantially more droplets being carried downstream by the airflow. However, the array of droplets created by the atomizer disc now contacted the shroud at the bottom edge of the shroud 22 resulting in droplet build up on the shroud as well as less coverage on the floor directly in front 2 to 3 feet of the extended-range spray applicator. Moving the atomizer assembly forward, with respect to the shroud air guide 22 resulted in fewer droplets being carried down range, while moving the atomizer assembly rearward resulted in more droplet build up on the lower half of the shroud and less coverage directly in front of the spray applicator. Accordingly, this version did not meet all acceptability criteria.

Example 4—Shroud Version 4

Figure 8A:
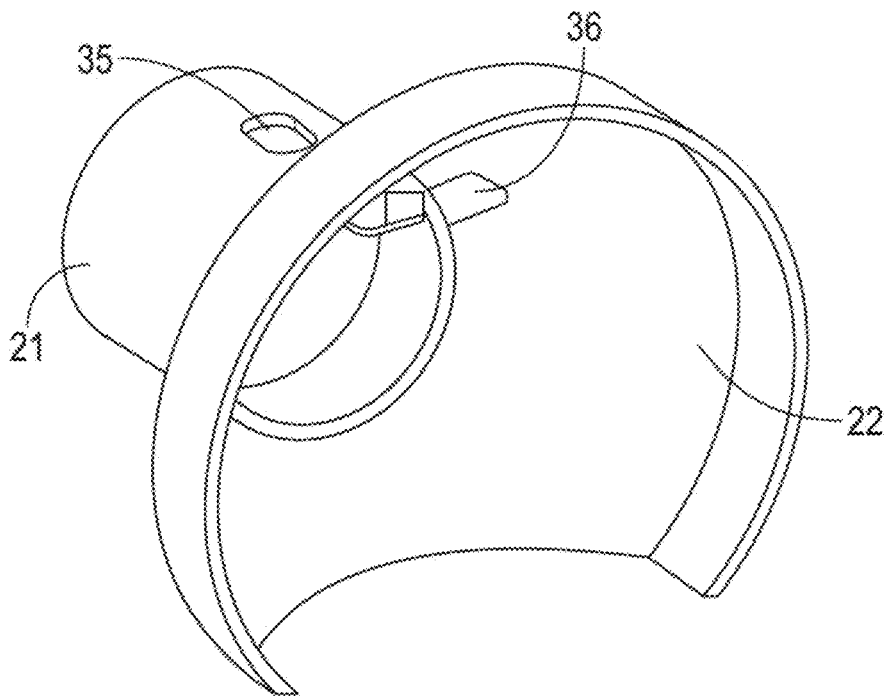
FIG. 8A shows a three-quarter side view of another head assembly 20.
Figure 8B:
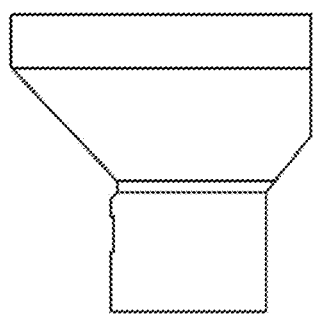
FIG. 8B shows a side cross-section of the head assembly 20 of FIG. 8A.
Figure 8C:
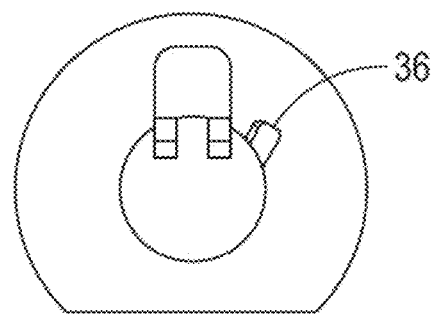
FIG. 8C shows a bottom cross-section of the head assembly 20 of FIG. 8A.
Figure 9A:
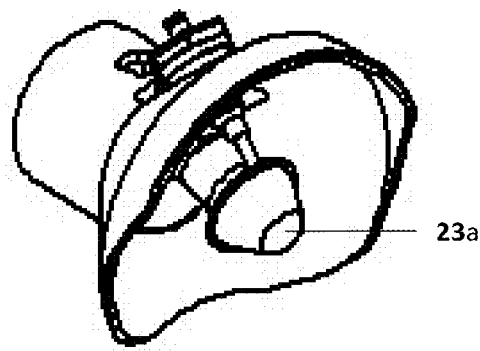
FIG. 9A shows a three-quarter side view of another head assembly 20.
Figure 9B:
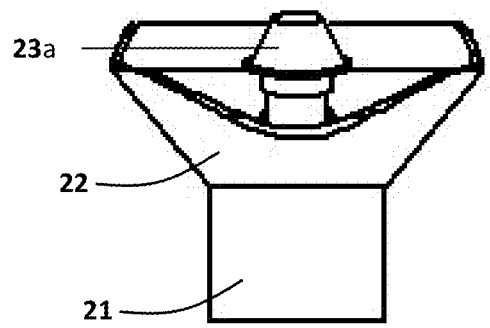
FIG. 9B shows a bottom view of the head assembly 20 of FIG. 9A.
Figure 9C:
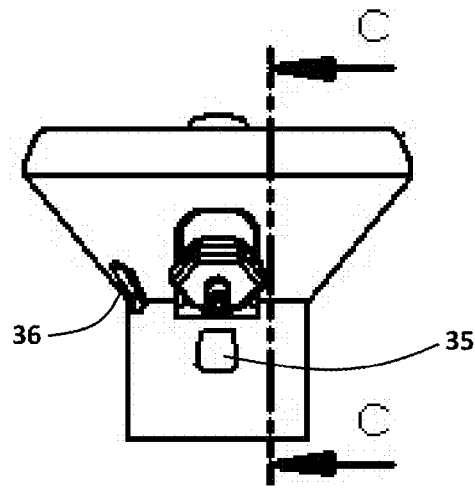
FIG. 9C shows a top view of the head assembly 20 of FIG. 9A, with a cross-section line drawn from air supply adapter to the far end of the shroud air guide.
Figure 9D:
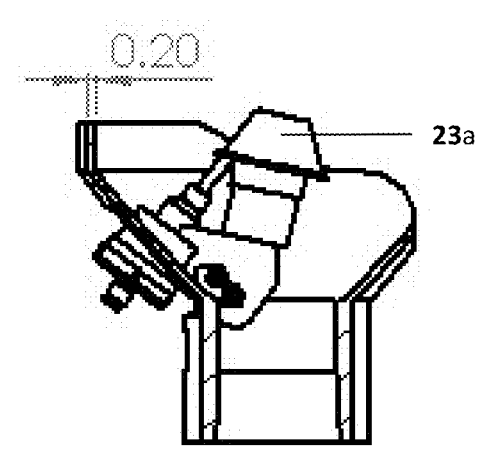
FIG. 9D shows a left cross-section view of the head assembly 20 of FIG. 9A, from the perspective of the cross-section line of FIG. 9C.
Figure 9E:
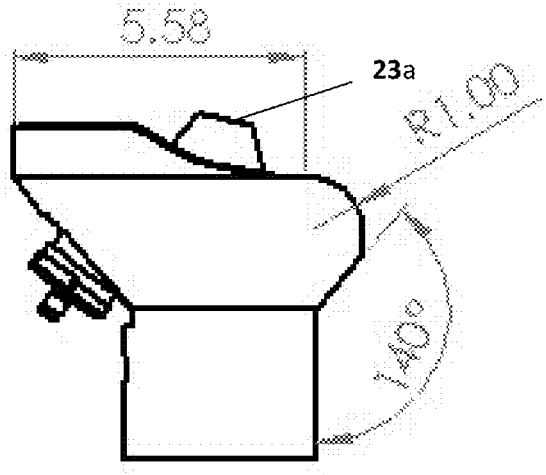
FIG. 9E shows a side view of the head assembly 20 of FIG. 9A.
Figure 9F:
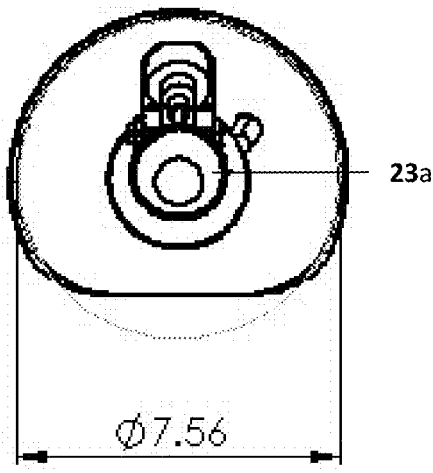
FIG. 9F shows a bottom view of the head assembly 2 of FIG. 9A.
Figure 10A:
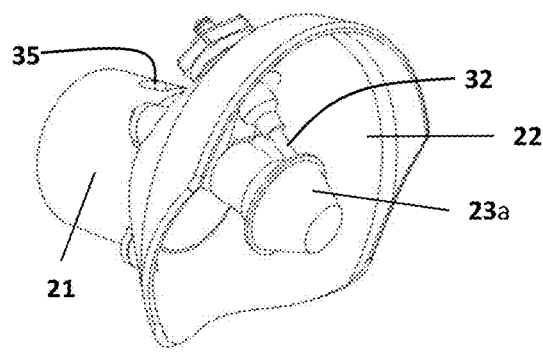
FIG. 10A shows a three-quarter side view of another head assembly 20. In this embodiment, the shroud air guide 22 and the air supply means adapter 21 are two separate pieces, which are configured to be reversibly connected to one another.
Figure 10B:
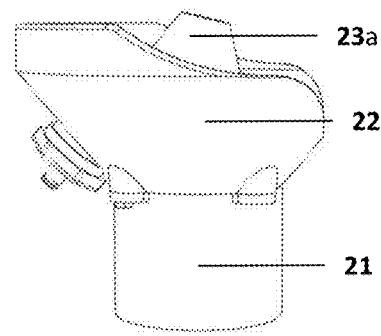
FIG. 10B shows a side view of the head assembly 20 of FIG. 10A.
Figure 10C:
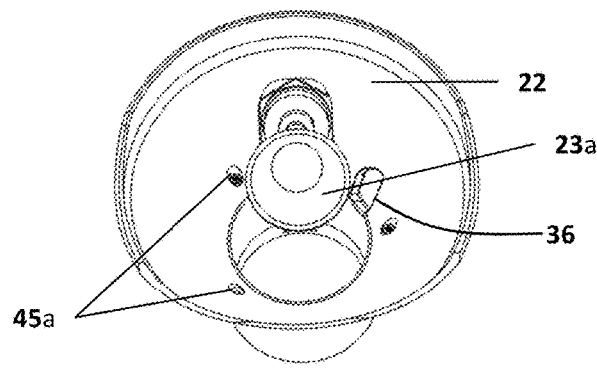
FIG. 10C shows a bottom view of the head assembly 20 of FIG. 10A.
Figure 10D:
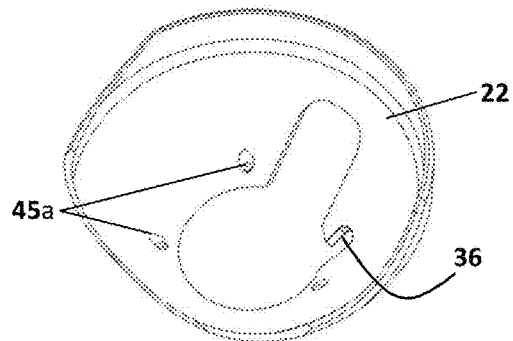
FIG. 10D shows the separated shroud air guide 22 and air supply means adapter 21 of the head assembly 20 of FIG. 10A. Shown are a separate shroud air guide 22 and air supply means adapter 21, which are configured to be reversibly attached to one another via any suitable attachment means, including via three holes 45a in the shroud air guide 22, which alignably correspond to three holes 45b in the air supply means adapter 21, such that a suitable attachment means e.g. a nut/bolt combination may be passed through the corresponding holes to fasten the shroud air guide 22 to the air supply means adapter 21.
Figure 10E:
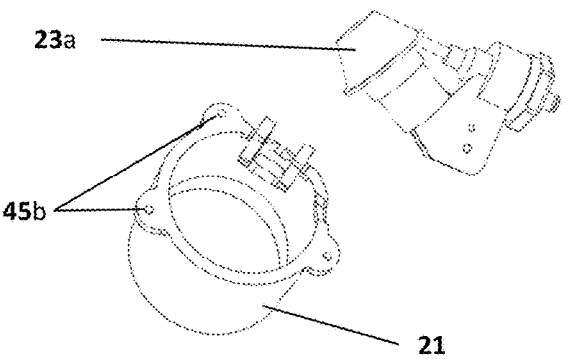
FIG. 10E shows a side/front view of the head assembly 20 of FIG. 10A.
Figure 10G:
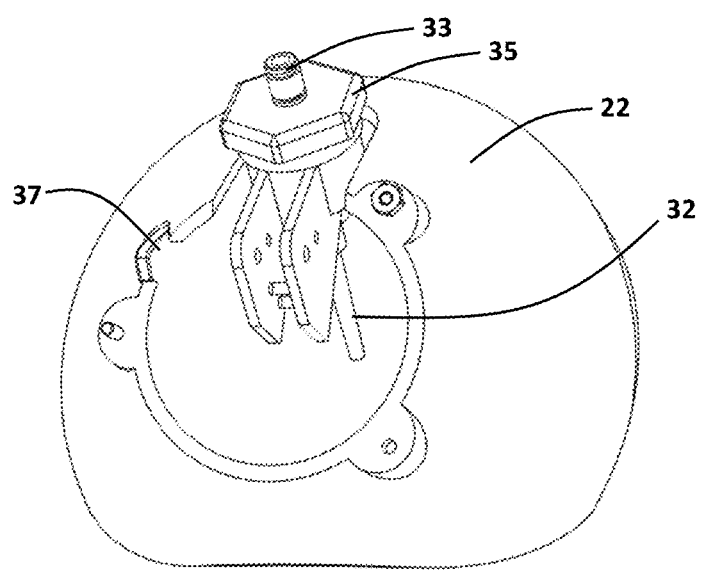
FIG. 10G shows a rear view of the head assembly 20 of FIG. 10A.

In Version 4 (FIGS. 8A-8C), the bottom of the shroud was modified to prevent droplet build up and provide better coverage directly in front of the device. These modifications also allowed the device to be placed on a flat surface when not in use and retain its upright position. A shroud extension ring 22a was added to capture a greater number of droplets with the airflow directed more substantially in the downstream direction. The shroud extension ring 22a defined a new diameter, D2 and an new angle, A1. While these modifications yielded better coverage of the vaccine or probiotic droplets directly in front of the spray applicator, droplets were unacceptably building up on the lower edges of the extension ring 22a. An access opening 37 was also added to allow easier access to the mounting hardware when removing the atomizer assembly for cleaning, repair etc. The adapter 21 was also decreased in length to about 2.8" to further improve the balance and ultimately the ergonomics of the spray applicator.

Example 5—Shroud Version 5

In Version 5 (FIGS. 9A-9F), the extension ring 22a and the diameter D3 were modified to prevent droplet build up. Component thickness was also increased to about 0.20" to improve durability.

Example 6—Shroud Versions 6 and 7

In Version 6, an advantageous single-shroud embodiment (FIGS. 10A-10D), the air supply means adapter 21 and shroud air guide 22 are separate pieces that may be attached to one another. Separation of the adapter and shroud provide additional manufacturing options, more versatility, and allows the shroud to be adapted to any air supply means. That said, the shroud air guide 22 could have a much larger diameter, including greater than 6 feet, which would allow the spray applicator to capture all the vaccine or probiotic droplets. However, such a device would not be very friendly to operate or produce. As such, a reasonable diameter was selected for the currently preferred head assembly 20.

In Version 7, Applicants have taken all the effective functional elements (e.g. two-piece design, shape, diameters, angles, etc.) of the Version 7 assembly 20, and adapted it to provide for the addition of secondary shrouds 62 having different geometries (as discussed above). The primary shroud 22 now comprises a slot 69 through which can pass the atomizers extenders 66. Without the extenders 66, or a suitable functional replacement therefor, it would not have been mechanically practical to add an additional shroud. Once the secondary shroud 62 was added to the spray applicator 100, Applicants found surprisingly that an even greater percentage of vaccine or probiotic droplets were being effectively delivered to the birds. This finding could not have been predicted in advance of the present disclosure, and was only made possible by the non-routine experimentation disclosed herein.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

Figure 3A:
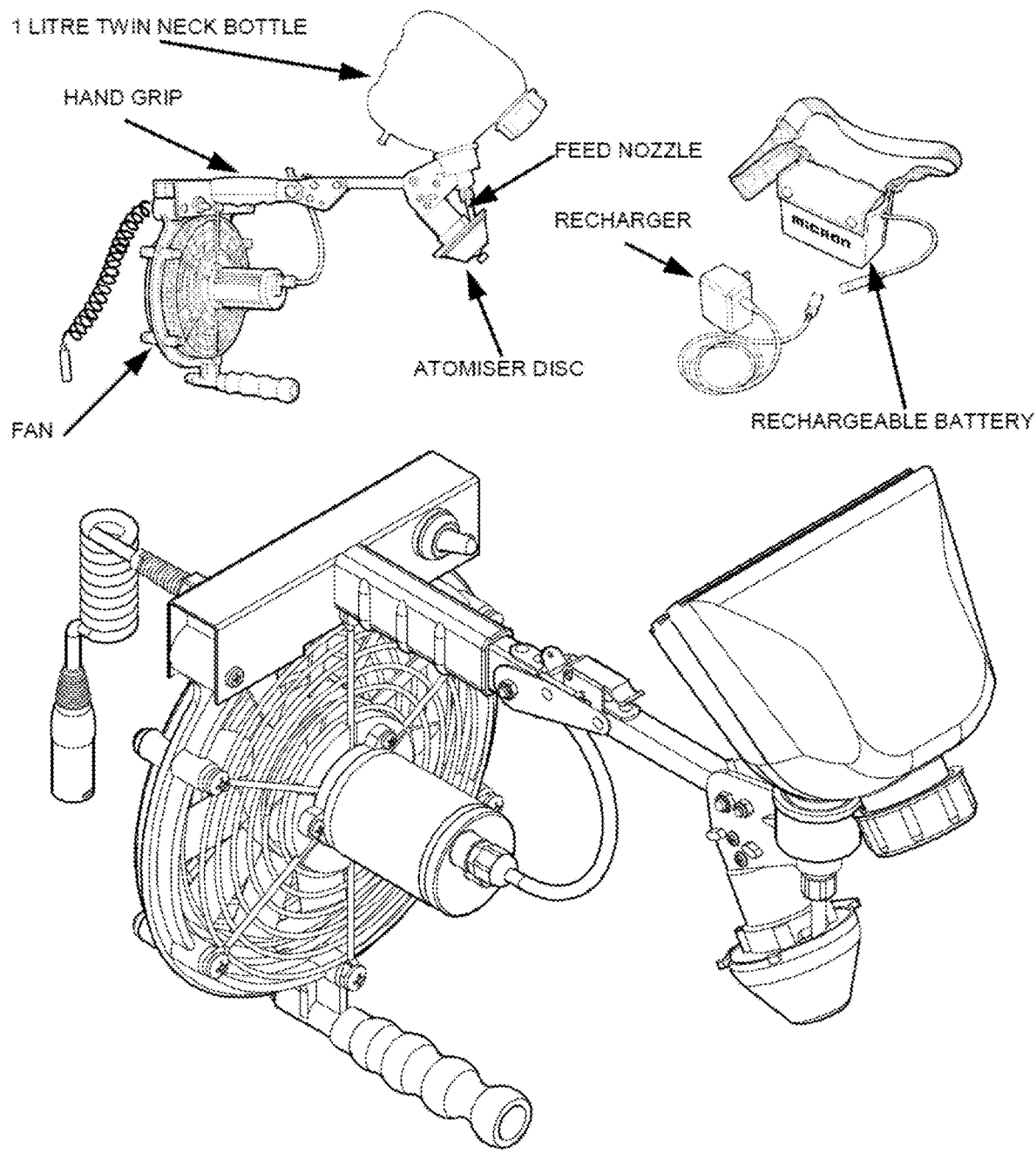
FIG. 3A shows the prior art UlvaVac™ sprayer made by Micron Sprayers for Merial.
Figure 3B:
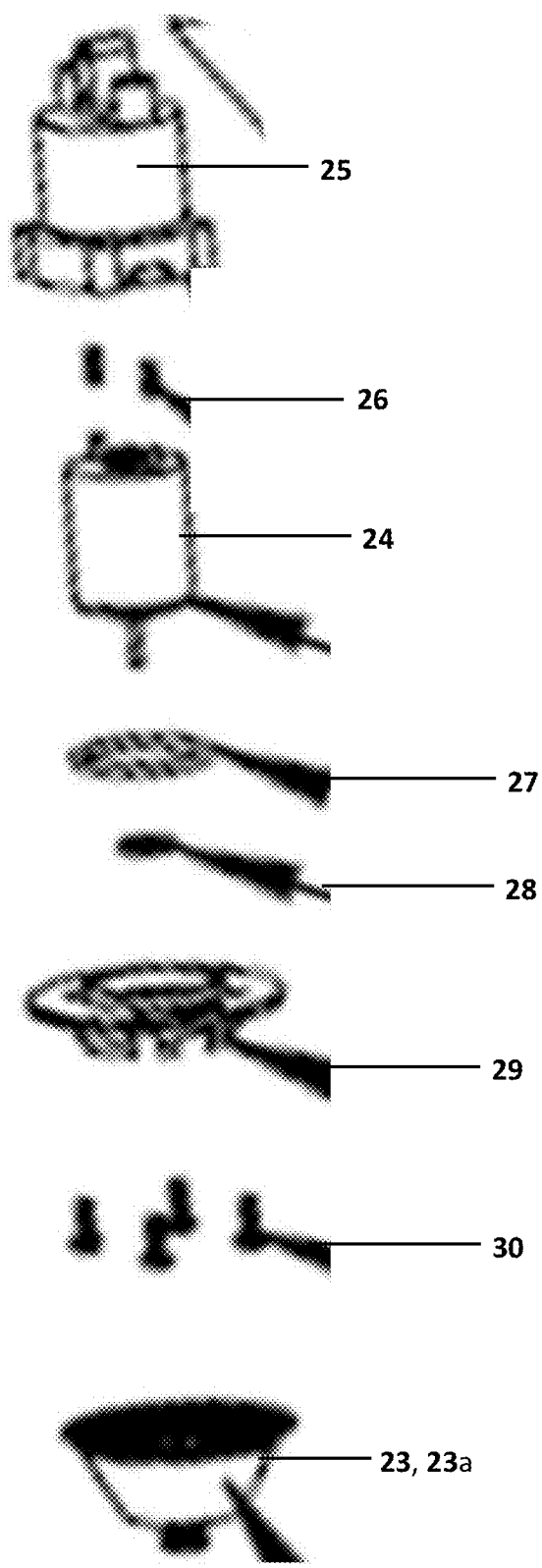
FIG. 3B shows an enlarged view of the exploded disc atomizer 23a operably connected to a disc motor 24 and disc motor housing 25. Shown are springs 26; o-rings 27, 28; a motor front plate 29; and motor front plate screws 30, for attaching the motor front plate to the motor housing 25.
Figure 4A:
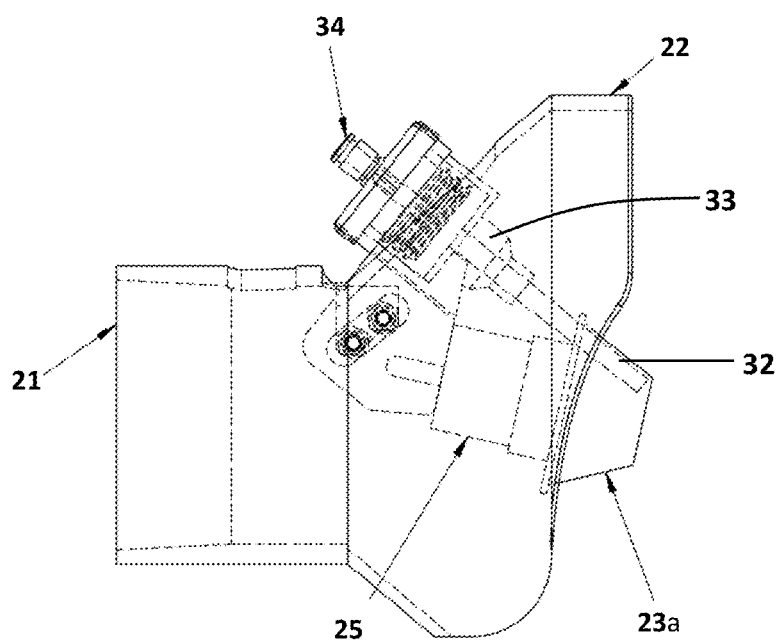
FIG. 4A shows a side view of the head assembly 20, having the shroud air guide 22, the nozzle 32 the rotating disc atomizer 23a, the disc atomizer motor housing 25, the quick connect hose adapter 34, and the air supply means adapter 21.
Figure 4B:
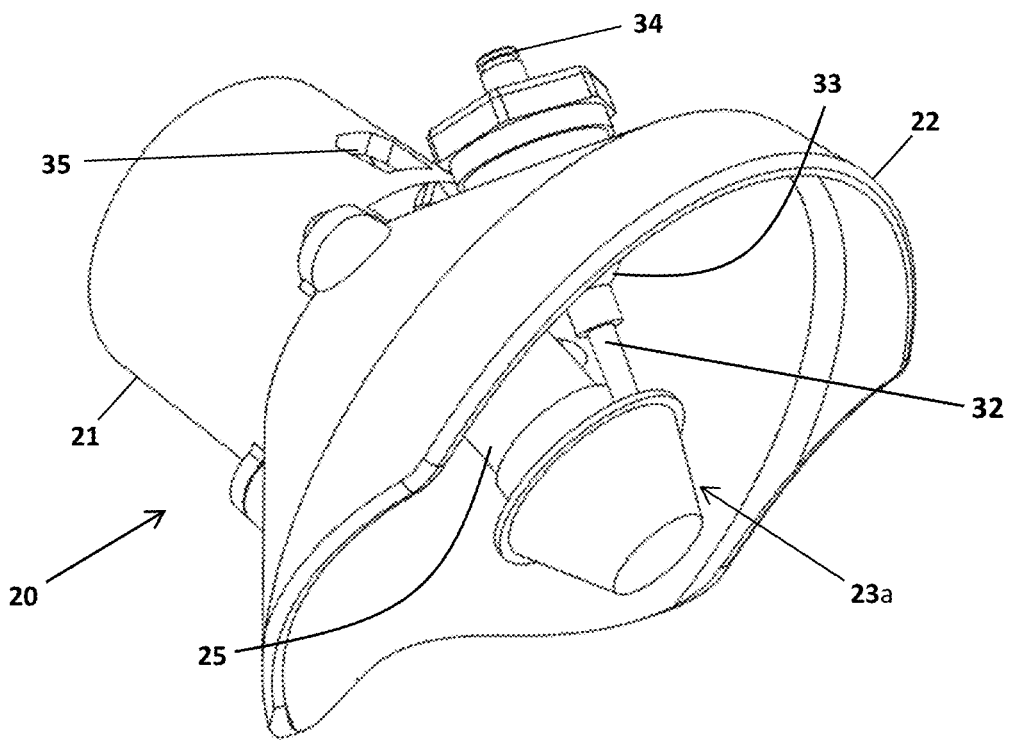
FIG. 4B shows a three-quarter front view of the head assembly 20, having the shroud air guide 22, the nozzle 32 the rotating disc atomizer 23a, the disc atomizer motor housing 25, the quick connect hose adapter 34, the air supply means adapter 21, and an air supply adapter attachment means 35, configured to allow for reversible and sealable attachment between the air supply means 10 and the air supply adapter means 21.
Figure 4C:
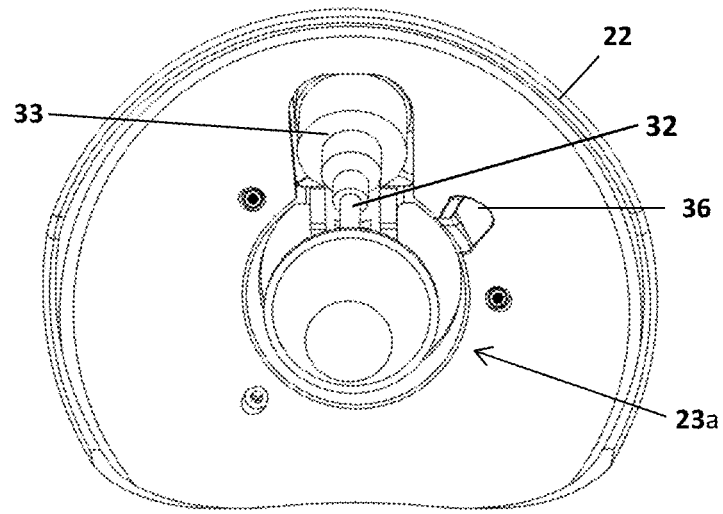
Figure 4D:
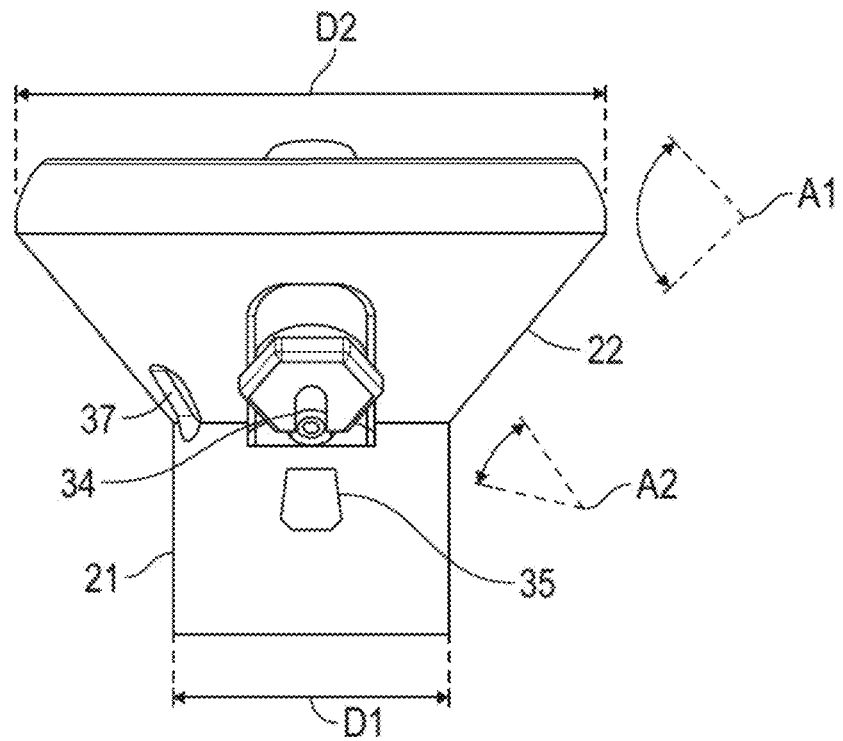
FIG. 4D shows a top view of the head assembly 20, showing the shroud air guide 22, the rotating disc atomizer 23a, the quick connect hose adapter 34, the air supply means adapter 21, and an air supply adapter attachment means 35 for reversibility attachably and sealably connecting the air supply means 10 to the air supply adapter means 21. Shown also is a first diameter D1, which is about equal in dimension to the diameter of the air supply conduit 11; a second diameter D2, which in this embodiment is the widest part of the shroud air guide 22. A1 defines an angle between a rear portion and a front portion of the shroud air guide 22; and A2 defines an angle between the rear portion of the shroud air guide 22 and a front portion of the air supply means adapter 21. The shroud also contains a cut-out 37 to accommodate a power supply wire/cable 38.
Figure 4E:
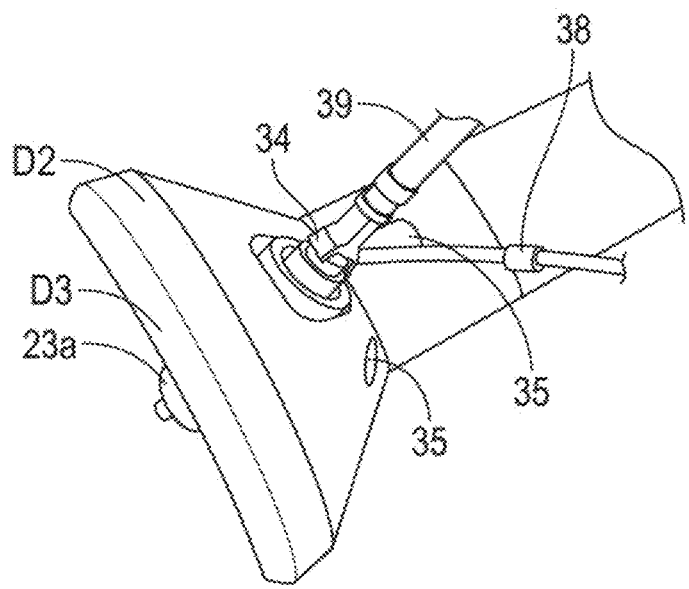
FIG. 4E shows a top view of the head assembly 20, showing the shroud air guide 22, the rotating disc atomizer 23a, the quick connect hose adapter 34, the air supply means adapter 21, and an air supply adapter attachment means 35 for reversibility attachably and sealably connecting the air supply means 10 to the air supply adapter means 21. Shown also is a first diameter D1, which is about equal in dimension to the diameter of the air supply conduit 11; a second diameter D2, which in this embodiment is the widest part of the shroud air guide 22; a third diameter D3, which is the diameter of the shroud air guide 22 at the end farthest away from the air supply adapter 21. A1 defines an angle between a rear portion and a front portion of the shroud air guide 22; and A2 defines an angle between the rear portion of the shroud air guide 22 and a front portion of the air supply means adapter 21. The shroud also contains a cut-out 37 to accommodate a power supply wire/cable 38.
Figure 5A:
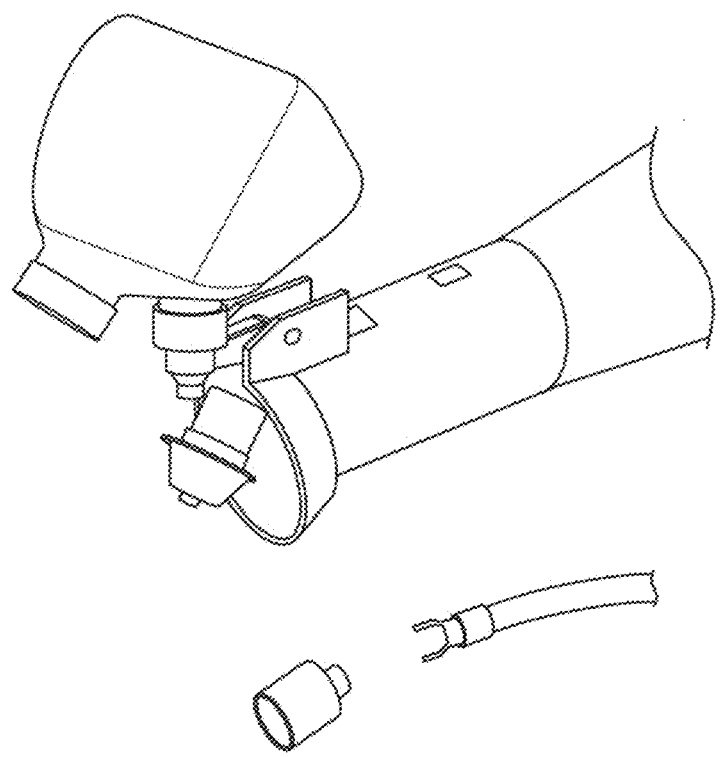
FIG. 5A shows a first version of an extended-range spray applicator having a first embodiment of a head assembly 20 operably connectable to a reservoir 40 and an air supply means 10.
Figure 5B:
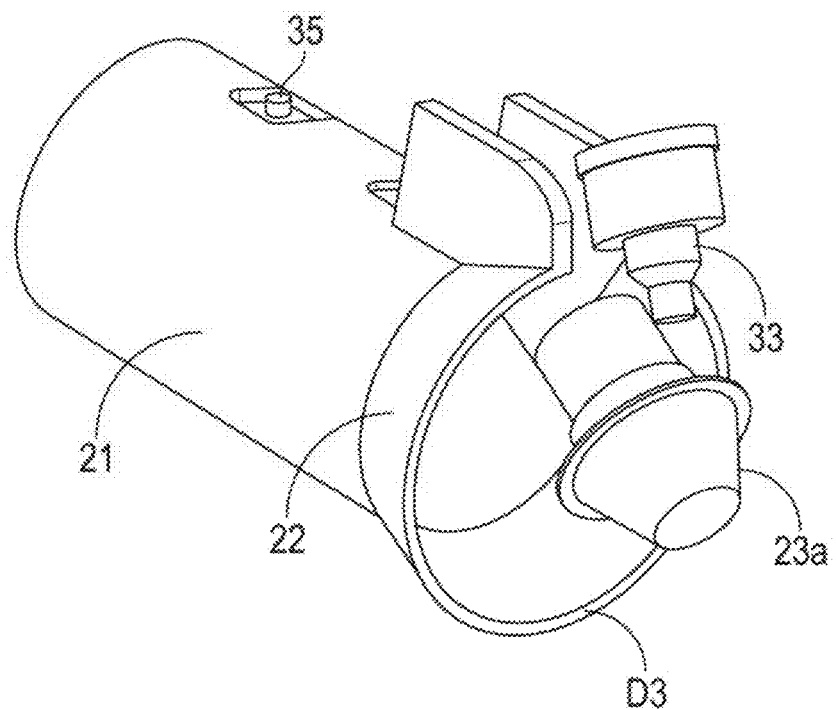
FIG. 5B shows a close-up of the head assembly 20 shown in FIG. 5A.
Figure 5C:
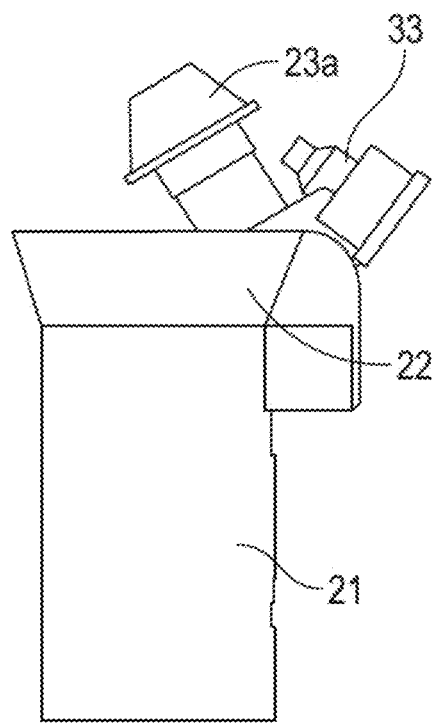
FIG. 5C shows a left cross-section view of the head assembly 20 shown in FIG. 5A.
Figure 5D:
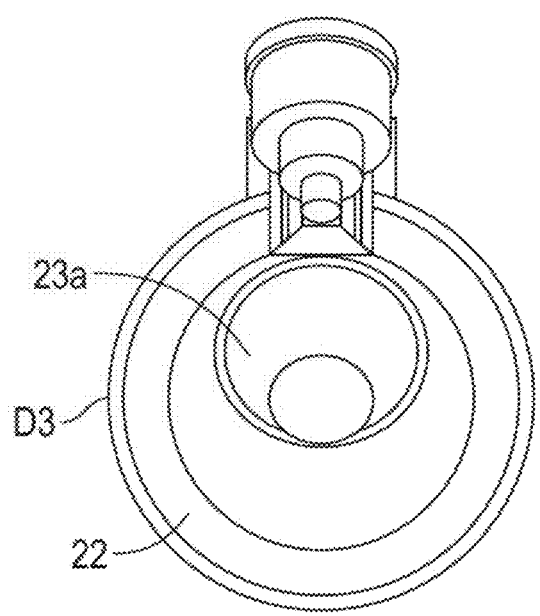
FIG. 5D shows bottom view of the head assembly 20 shown in FIG. 5A.

Example 7—High Speed Video and Drop Size Characterization Confirms Uniform and Acceptable Droplet Size is Maintained Up to at Least 20 Feet High-speed video and drop size characterization of two droplet dispersion devices used in a vaccine delivery application was conducted. The two rotary atomizers evaluate are: 1 Micron ULVAFAN/ULVAPAK-MK2 FIG. 3A ultra-low volume rotary atomizer with battery operation and an 2 ULVAPAK/Hybrid leaf blower assembly i.e. an extended-range spray applicator according to the disclosure and as depicted in FIG. 1 outfitted with a battery powered leaf-blower air supply means unit to deliver spray droplets at a significant distance, including at least about 5 or about 10 meters, away from the operator. A comprehensive evaluation was carried out to investigate the spray characteristics at various distances with an objective to understand the old and new design performance.

Figure 13:
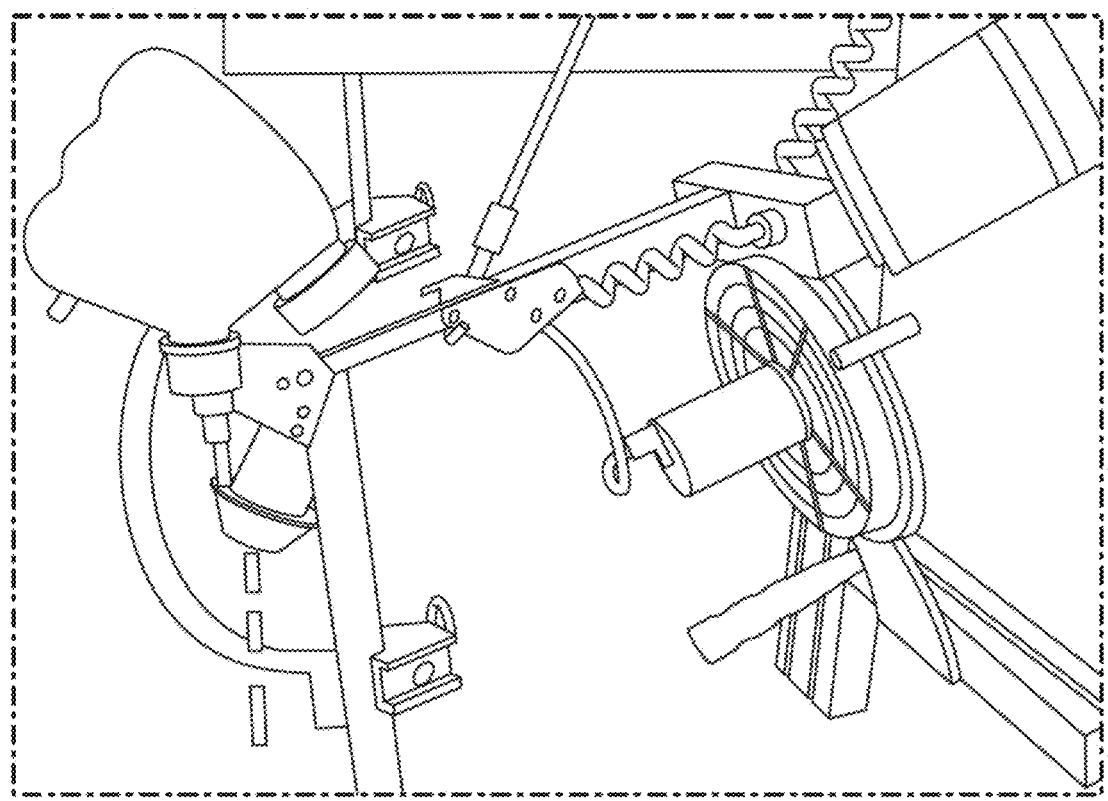
FIG. 13 shows the ULVAFAN/ULVAPAK-MK2 with Olympus i-SPEED TR High Speed Video Camera.
Figure 14:
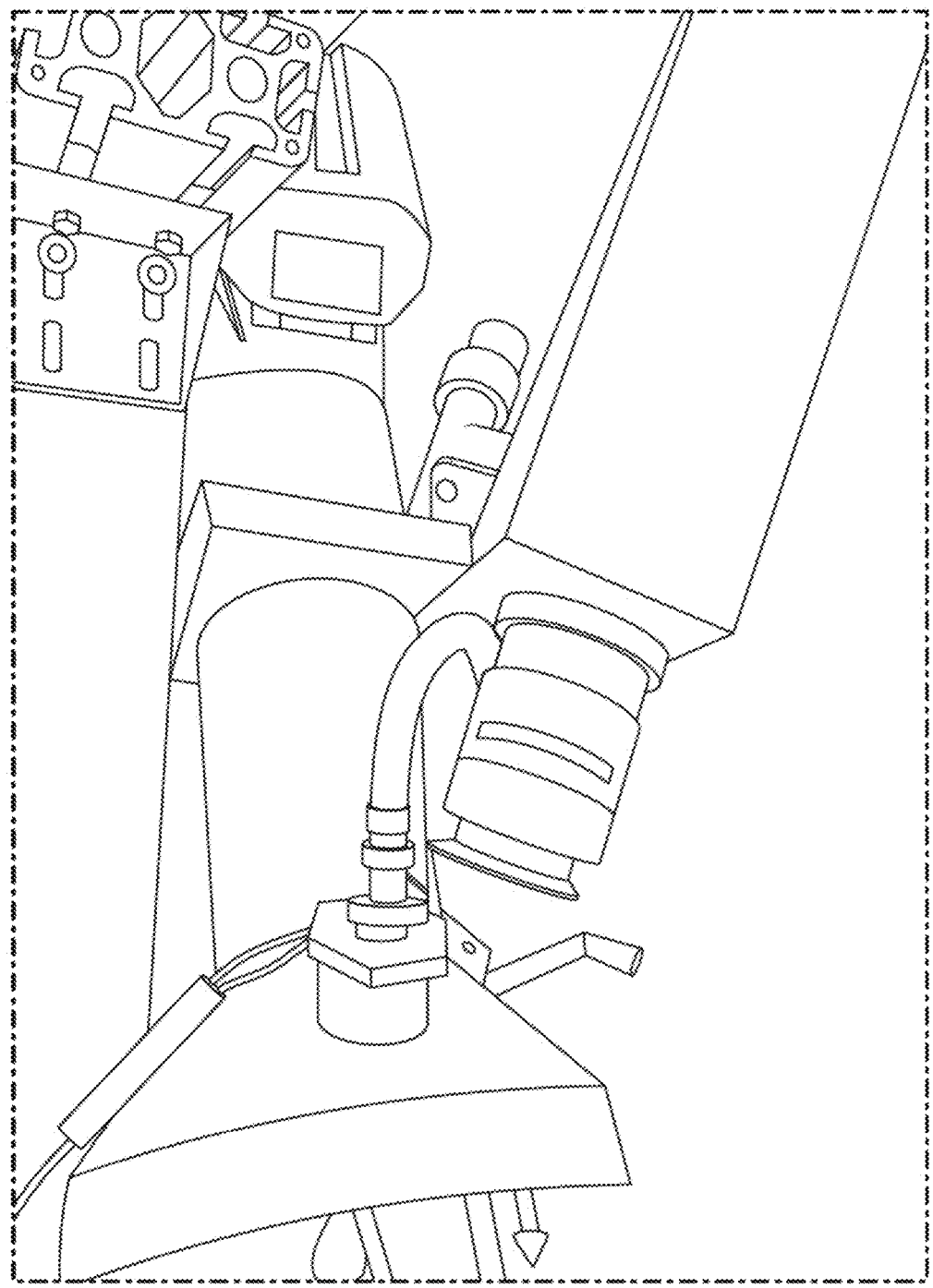
FIG. 14 shows an extended-range spray applicator with Olympus i-SPEED TR High Speed Video Camera.

Test Setup. An Olympus i-SPEED TR high-speed video camera was used for capturing video during this test. This camera is designed for research and development usage where the objective is to capture high quality video images for subsequent review and analysis. With an acquisition rate of up to 2,000 frames per second at a full resolution of 1280×1024, and a top speed of 10,000 fps, the camera is suitable for the vast majority of spray analysis and research testing. The test setup consisted of fabricating a holding bracket for the ULVAFAN/ULVAPAK-MK2 for high-speed videography. The extended-range spray applicator was held in place with a four-inch pipe clamp on a three-axis traverse. Three-axis traverse allowed final adjustments to achieve clean field of view for high-speed videography FIG. 13 and FIG. 14. All testing was conducted using water at ambient lab conditions i.e. approximately 20° C.

Figure 15:
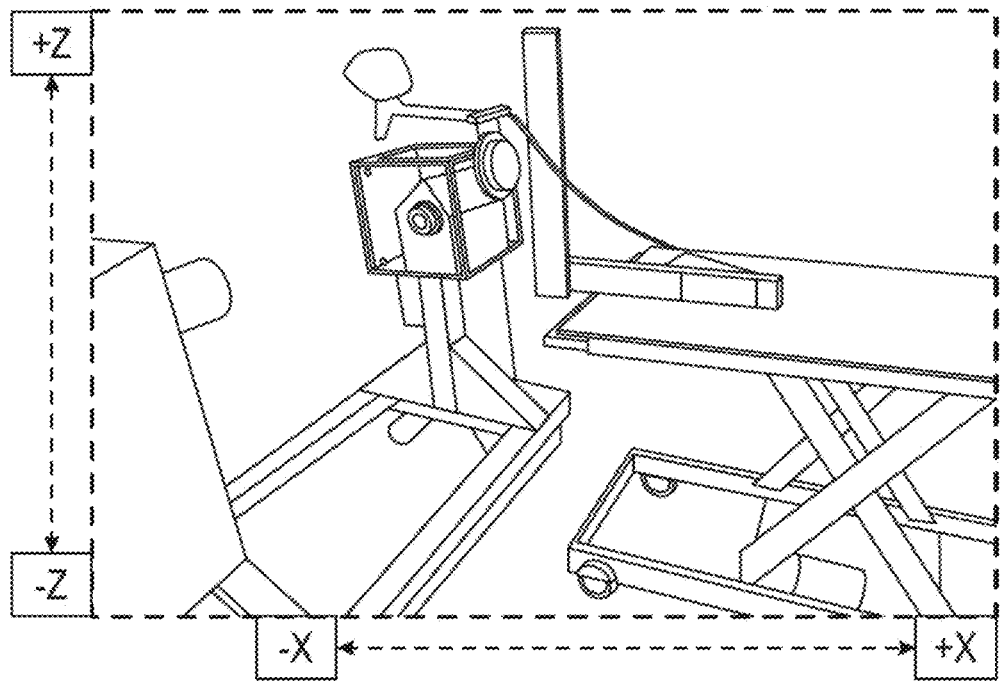
FIG. 15 shows an ULVAFAN/ULVAPAK-MK2 with Sympatec Laser Diffraction Particle Analyzer.
Figure 16:
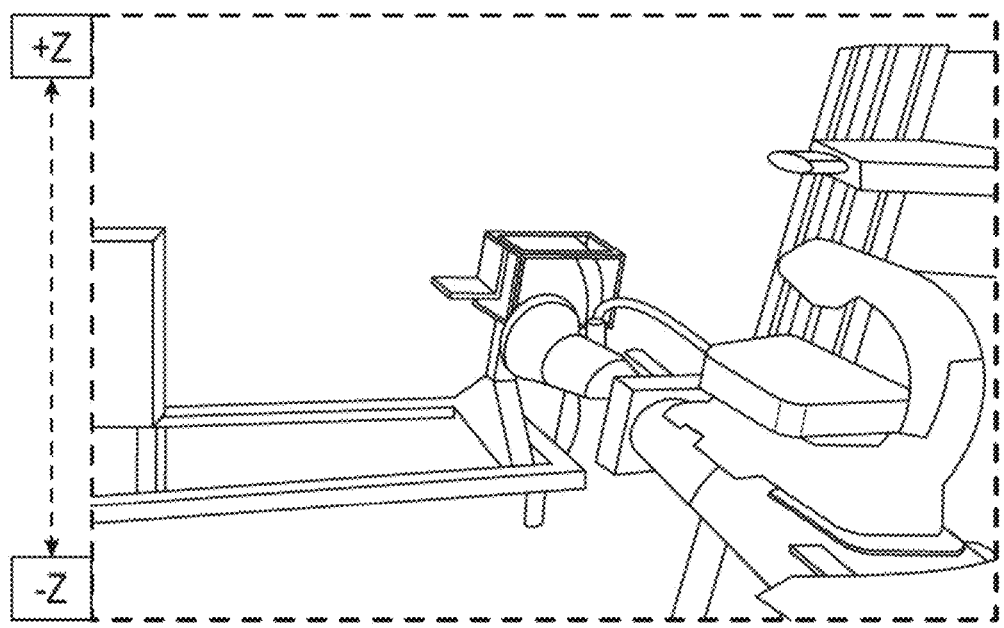
FIG. 16 shows an extended-range spray applicator with Sympatec Laser Diffraction Particle Analyzer.

Drop Size Measurement. The Sympatec HELOS Particle Analyzer was used to acquire drop size measurements for this test FIG. 15 and FIG. 16. The Sympatec unit is a laser diffraction instrument that measures drop size based on the diffraction pattern of the laser light encountering droplets passing through the analyzer's sampling area a wide laser beam. The scattered light intensity distribution was measured using a multi-element semicircular photo-detector housed in the receiver unit left side in FIGS. 15 and 16. Testing was performed using an R6 lens setup. This lens configuration allowed a measurement range of 0.5-9 µm to 1750 µm. All droplets were given a size within a bin-range, the smallest bin of which covers the 0.5-9 µm range, and the largest of which can detect droplets up to 1750 µm. The collected drop size distributions were then used to generate drop size statistics, such as the Median Volume Diameter Dv0.5 or MVD. To characterize the spray performance consistently a typical spray scanning technique was implemented by attaching the atomizer assemblies to an electric cart. The atomizers were traversed vertically in +/−Z directions spraying perpendicular through the measurement area. For characterization at various distances in the +X direction a measuring tape was used as a marker where the zero of the tape was at the center of the measurement area bottom of FIGS. 15 and 16.

The reservoir level was filled to full at the beginning of each test to reduce the pressure-head changes introduced by water displaced during testing. The battery was charged to full status indicated as solid green on the extended-range spray applicator charger.

For drop size characterization of ULAVPAK/Hybrid Assembly extended-range spray applicator, the grey shroud was used. The tank level was filled to full before each test to reduce the gravity pressure-head changes by water displaced during testing. An external 12V DC power source with an on/off toggle switch fabricated by Spraying Systems Co® and used to power the spinning disc atomizer. The $D_{V0.1}$, $D_{V0.5}$, and $D_{V0.9}$ diameters as defined below were used to evaluate the drop size data in microns µm. The drop size terminology is defined below, and more information can be found in Understanding Drop Size, Bulletin 459c, available at the following link: www.spray.com/literature_pdfs/B459C_Understanding_Drop_Size.pdf.

$D_{V0.1}$: A value where 10% of the total volume or mass of liquid sprayed is made up of drops with diameters smaller or equal to this value.

$D_{V0.5}$: Volume Median Diameter also known as VMD. A means of expressing drop size in terms of the volume of liquid sprayed. The VMD is a value where 50% of the total volume or mass of liquid sprayed is made up of drops with diameters larger than the median value and 50% smaller than the median value. This diameter is used to compare the change in drop size on average between test conditions.

$D_{32}$: Sauter Mean Diameter also known as SMD is a means of expressing the fineness of a spray in terms of the surface area produced by the spray. The Sauter Mean Diameter is the diameter of a drop having the same volume to surface area ratio as the total volume of all the drops to the total surface area of all the drops.

$D_{V0.9}$: A value where 90% of the total volume or mass of liquid sprayed is made up of drops with diameters smaller or equal to this value.

$D_{V0.99}$: A value where 99% of the total volume or mass of liquid sprayed is made up of drops with diameters smaller or equal to this value.

Figure 17:
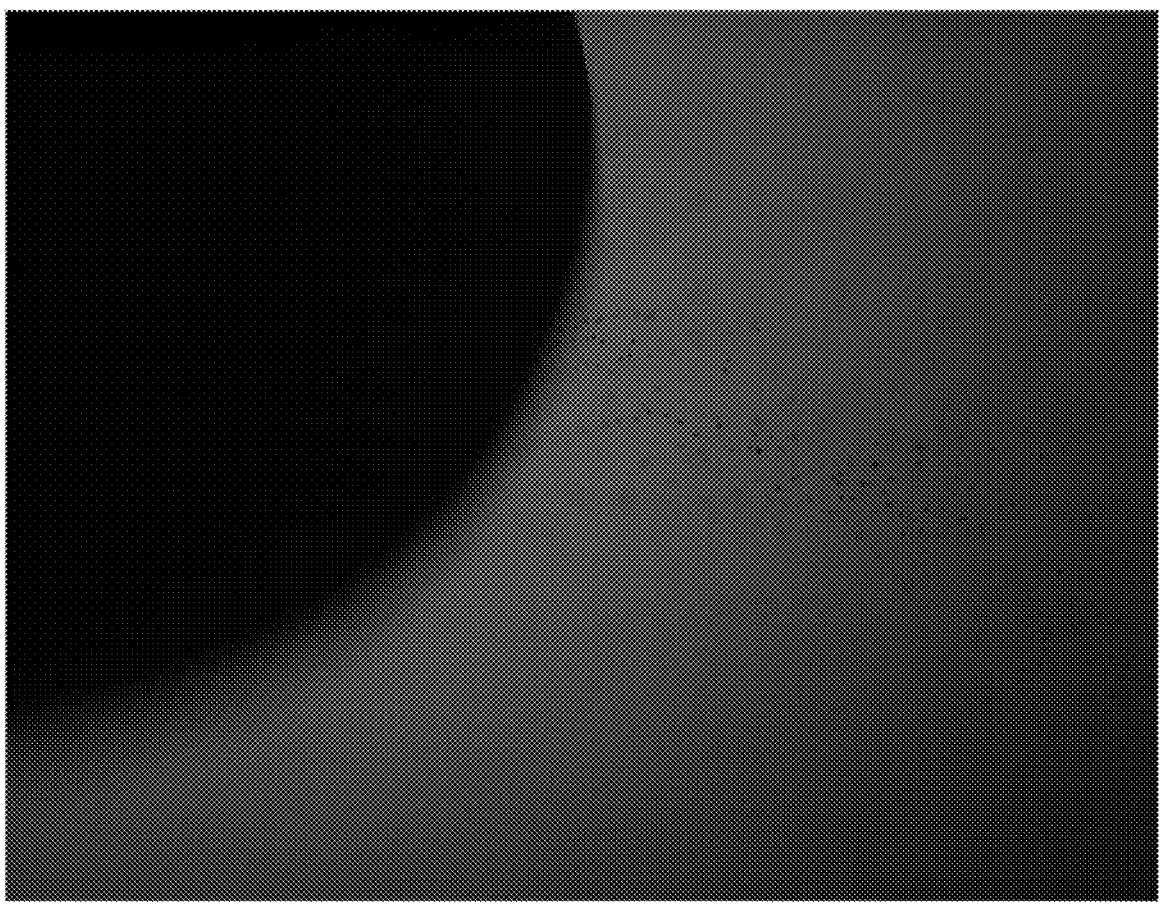
FIG. 17 shows an ULVAFAN/ULVAPAK-MK2 High Speed Image.
Figure 18:
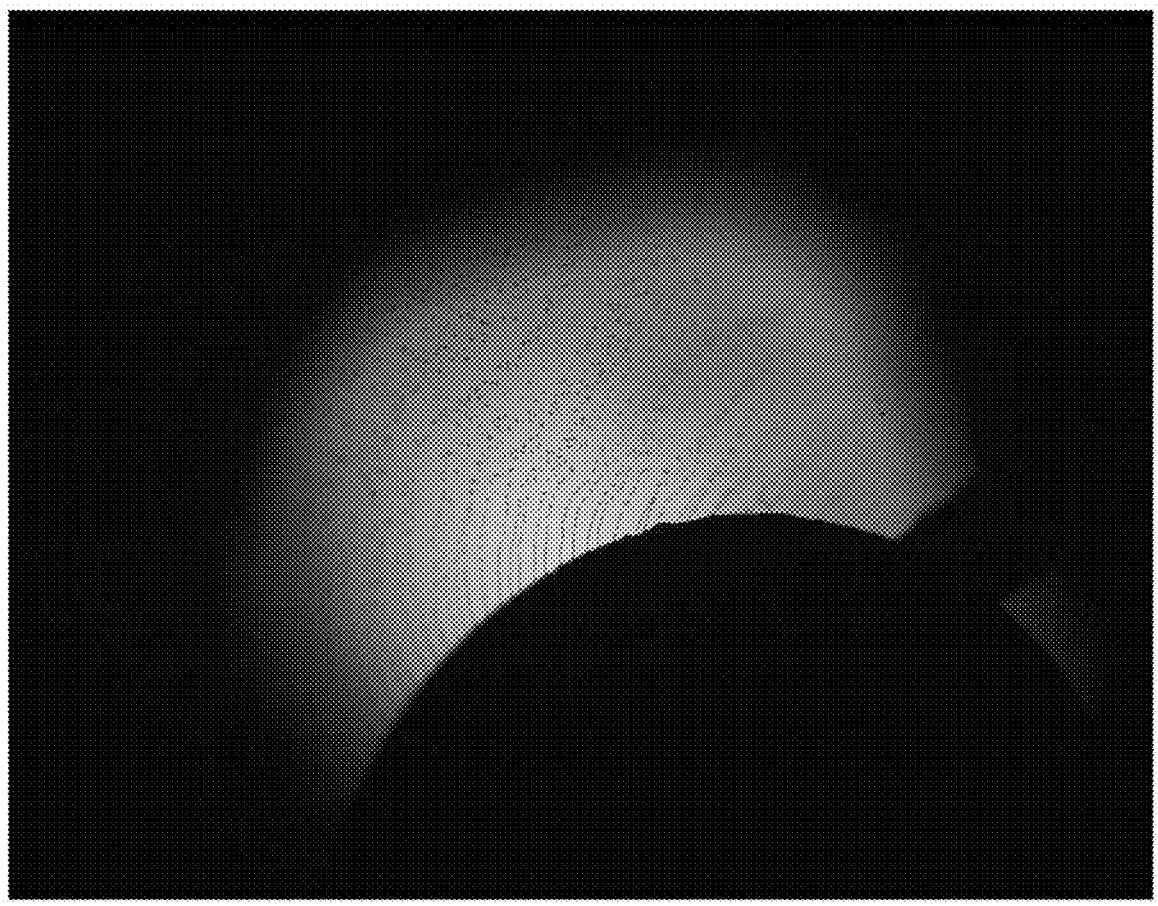
FIG. 18 shows an extended-range spray applicator High Speed Image.

Test Results & Analysis. High-speed video was acquired near the exit of the spinning disk atomizer to visualize the formation of droplets and the interaction of the droplets with the airstream. Sympatec drop size testing was conducted at multiple downstream distances to assess the drop size characteristics as well as the relative density of the spray cloud. All testing data was collected at one speed for ULVAFAN/ULVAPAK MK2 atomizer with the onboard on/off switch. For the extended-range spray applicator Hybrid Assembly, data was collected with the blower fan triggered to max with the atomizer powered by an external 12V DC power with 200 milliamps. Representative screen shots of the high-speed video recording of ULVAFAN/ULVAPAK MK2 FIG. 17 and Hybrid Assembly FIG. 18, highlight the atomization process of droplets at the exit of spinning disk geometry. Videos have been produced and may be submitted as electronic amendments to this application.

The second phase of the tests was to characterize the ULVAFAN/ULVAPAK MK2 and the ULVAPAK/Hybrid Assembly for drop size using the Sympatec laser diffraction instrument at many downstream distances from the atomizers. The maximum distance of data collection depended on each blower fan's ability to push a sufficient quantity of droplets downstream. The spray plume was scanned a minimum of two times for data collected at each distance. A straight average method was used to obtain the final results, which are provided in Table 2.

Figure 19:
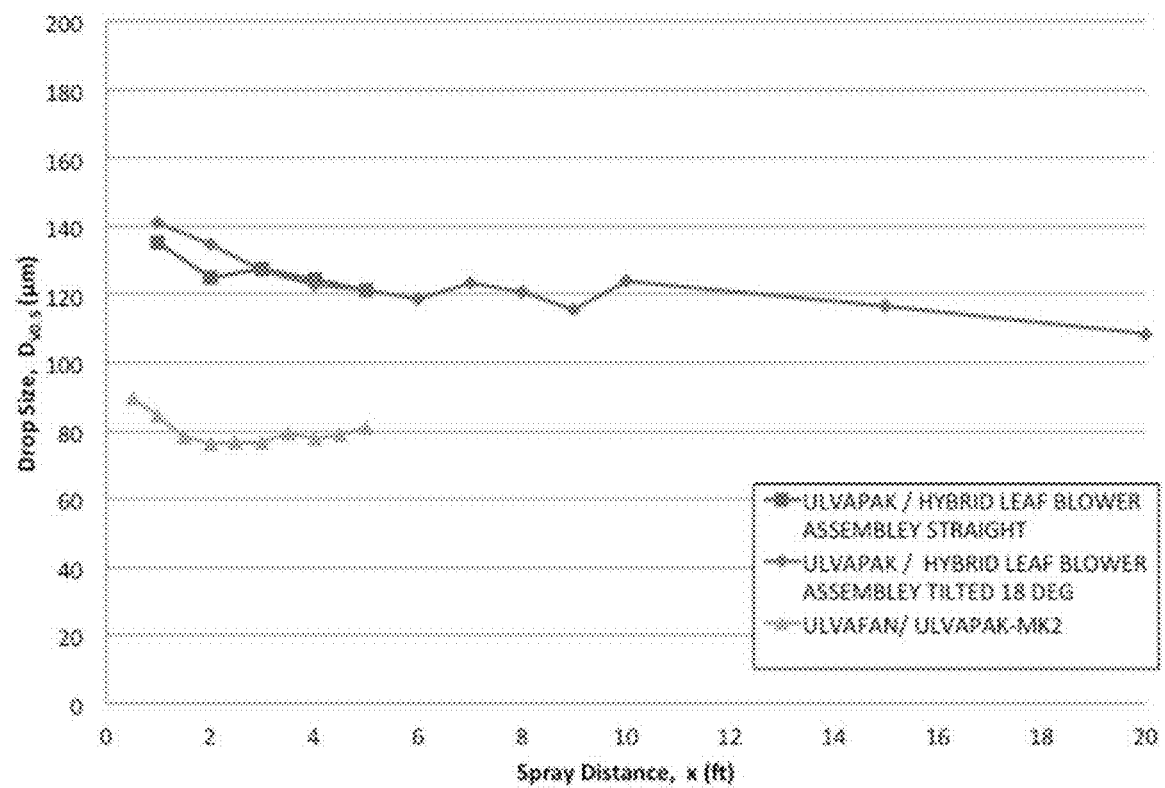
FIG. 19 is a graph showing MVD of atomizers over various distances in X direction.

All drop size measurements acquired for the ULVAFAN/ULVAPAK MK2 atomizer were at constant speed, a step of a half-foot over a maximum distance of five feet was collected Table 2. The MVD data recorded under 100 µm for ULVAFAN/ULVAPAK MK2 is consistent over several distances, a low concentration of droplets at further distances provided a maximum measurement distance of 5 feet FIG. 19.

For drop size collection of ULVAPAK/Hybrid Assembly, the blower fan trigger was pressed at maximum speed, with power supplied directly to the atomizer. The system was allowed to stabilize for few seconds prior each scan for drop size data collection.

TABLE 2

High Speed Videography Data

| Nozzle Name | Gravity Feed Water Supply Height in | Spray Distance ft | $D_{v0.1}$ | $D_{32}$ | $D_{V0.5}$ | $D_{V0.99}$ |
|---|---|---|---|---|---|---|
| Micron UlvaFan/UlvaPak-MK2 | Onboard Tank Attached | 0.5 | 52 | 81 | 90 | 142 |
| | | 1 | 50 | 78 | 84 | 141 |
| | | 1.5 | 48 | 73 | 78 | 128 |
| | | 2 | 47 | 71 | 76 | 125 |
| | | 2.5 | 46 | 71 | 77 | 127 |
| | | 3 | 46 | 71 | 77 | 131 |
| | | 3.5 | 47 | 72 | 79 | 130 |
| | | 4 | 46 | 71 | 78 | 127 |
| | | 4.5 | 46 | 72 | 78 | 129 |
| | | 5 | 47 | 74 | 81 | 135 |
| Extended-range spray applicator hybrid blower tilted up 18° | 6" from nozzle inlet | 1 | 86 | 124 | 135 | 197 |
| | | 2 | 80 | 115 | 125 | 184 |
| | | 3 | 77 | 115 | 128 | 187 |
| | | 4 | 73 | 110 | 124 | 181 |
| | | 5 | 69 | 107 | 121 | 177 |
| Extended-range spray applicator hybrid blower tilted up 18° | 6" from nozzle inlet | 1 | 95 | 133 | 141 | 201 |
| | | 2 | 90 | 128 | 135 | 201 |
| | | 3 | 83 | 119 | 127 | 191 |
| | | 4 | 80 | 115 | 123 | 188 |
| | | 5 | 78 | 113 | 121 | 187 |
| | | 6 | 75 | 109 | 119 | 186 |
| | | 7 | 69 | 108 | 123 | 184 |
| | | 8 | 73 | 110 | 121 | 191 |
| | | 9 | 70 | 106 | 115 | 184 |
| | | 10 | 76 | 113 | 124 | 195 |

During data collection, it was observed that the angled nozzle on the shroud assembly was generating an obstruction at the blower exit. The majority of the forced air was directed so that it was concentrated over the lower-half portion of the spray plume. The top half portion of the spray was unaffected by the forced air which allowed some particles to follow their natural path to ground.

What is claimed:

1. An extended-range spray applicator comprising:

an air supply, primary shroud mounted on and in fluid communication with the air supply, a liquid atomizer mounted on the air supply, and;

a secondary shroud detachably positioned between the primary shroud and the liquid atomizer, and wherein the liquid atomizer is laterally adjustable with respect to the air supply.

2. The spray applicator of claim 1, wherein the primary and secondary shrouds comprise slots through which one or more extenders pass.

3. The spray applicator of claim 2, wherein the atomizer is fixedly connected to the one or more extenders.

4. The spray applicator of claim 2, wherein the atomizer is adjustably connected to the one or more extenders, such that a user may direct the atomizer upward or downward, with respect to the direction of air flow.

5. The spray applicator of claim 1, wherein the liquid atomizer being laterally adjustable with respect to the air supply allows a user to position the atomizer such that it is either nearer to, or farther from, the air supply.

6. The spray applicator of claim 1, wherein both the primary and secondary shrouds comprise a plurality of spacers, which are configured to allow the shrouds to be reversibly connected to one another.

7. The spray applicator of claim 6, wherein each shroud comprises 4 spacers.

8. The spray applicator of claim 1, wherein the air supply comprises an adapter that is cylindrical and comprises a means for lockably attaching a head assembly to an air supply portion of the spray applicator.

9. The spray applicator of claim 8, further comprising a battery housing, situated atop the head assembly, and configured to receive and house a rechargeable battery, which supplies electricity to an atomizer motor.

10. The spray applicator of claim 1, wherein the liquid atomizer is a rotary disc atomizer, which is mechanically connected to a disc atomizer motor, which is housed within a motor housing, which is fixedly connected to a disc atomizer assembly frame.

11. The spray applicator of claim 8, wherein the liquid atomizer comprises a rotary disc atomizer, for transforming liquid into sub-millimeter-sized droplets; wherein the rotary disc atomizer is situated centrally within the primary and secondary shrouds;

at least two extenders, for attaching the rotary disc atomizer to the head assembly;

a motor, mechanically connected to the rotary disc atomizer; and a battery receptacle, for holding a battery, which is electrically connected to the motor.

12. The spray applicator of claim 11, wherein the secondary shroud has a conical angle of about 30°.

13. The spray applicator of claim 11, wherein at least one shroud is characterized by having at least three diameters, D1, D2 and D3, and at least two angles, A1 and A2.

14. The spray applicator of claim 13, wherein D1 is at least about 30% to about 50% smaller than D2; and wherein D2 is about equal to or is about 10% smaller than D3.

15. The spray applicator of claim 14, wherein A1 is between about 90° and about 145°; and wherein A2 is between about 130° and 160°.

* * * * *